United States Patent
Nicolls et al.

(10) Patent No.: US 10,220,009 B2
(45) Date of Patent: Mar. 5, 2019

(54) HIF-1 MODULATOR PAINT FORMULATION AND USES THEREOF

(71) Applicants: The Board of Trustees of the Leland Stanford Junior University, Stanford, CA (US); THE UNITED STATES OF AMERICA AS REPRESENTED BY THE DEPARTMENT OF VETERANS AFFAIRS, Washington, DC (US); THE JOHNS HOPKINS UNIVERSITY, Baltimore, MD (US)

(72) Inventors: Mark R. Nicolls, Palo Alto, CA (US); Jayakumar Rajadas, Cupertino, CA (US); Geoffrey C. Gurtner, Woodside, CA (US); Xinguo Jiang, Palo Alto, CA (US); Gundeep Dhillon, Stanford, CA (US); Gregg L. Semenza, Reisterstown, MD (US)

(73) Assignees: The Board of Trustees of the Leland Stanford Junior University, Stanford, CA (US); The Johns Hopkins University, Baltimore, MD (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/424,994

(22) PCT Filed: Aug. 30, 2013

(86) PCT No.: PCT/US2013/057544
§ 371 (c)(1),
(2) Date: Feb. 27, 2015

(87) PCT Pub. No.: WO2014/036414
PCT Pub. Date: Mar. 6, 2014

(65) Prior Publication Data
US 2015/0196512 A1   Jul. 16, 2015

Related U.S. Application Data

(60) Provisional application No. 61/695,188, filed on Aug. 30, 2012.

(51) Int. Cl.
| *A61K 9/51* | (2006.01) |
| *A61K 45/06* | (2006.01) |
| *A61K 31/164* | (2006.01) |
| *A61K 31/436* | (2006.01) |
| *A61K 31/4196* | (2006.01) |
| *A61K 31/4412* | (2006.01) |

(52) U.S. Cl.
CPC .......... *A61K 31/164* (2013.01); *A61K 9/5123* (2013.01); *A61K 9/5138* (2013.01); *A61K 9/5146* (2013.01); *A61K 9/5161* (2013.01); *A61K 9/5169* (2013.01); *A61K 31/4196* (2013.01); *A61K 31/436* (2013.01); *A61K 31/4412* (2013.01); *A61K 45/06* (2013.01)

(58) Field of Classification Search
CPC .................................................... A61K 31/164
USPC ........................................................ 424/489
See application file for complete search history.

(56) References Cited

U.S. PATENT DOCUMENTS

| 4,559,298 A | * | 12/1985 | Fahy | ........................ A01N 1/02 |
| | | | | 435/1.2 |
| 5,635,159 A | * | 6/1997 | Fu Lu | ..................... A61K 9/008 |
| | | | | 424/45 |
| 6,509,380 B1 | | 1/2003 | Walker | |
| 2011/0064794 A1 | * | 3/2011 | Deng | ................... A61K 9/1075 |
| | | | | 424/450 |

FOREIGN PATENT DOCUMENTS

| WO | 2007026028 A2 | 3/2007 |
| WO | WO 2009/092291 | * 7/2009 |

OTHER PUBLICATIONS

Kennedy (J Clin Invest. Apr. 1989; 83(4):1326-1335.).*
Bugaj (Journal of Photochemistry and Photobiology B: Biology 83 (2006) 94-97).*
Hershko, "Iron chelators in medicine.", Mol. Aspects Med. (1992), 13(2):113-65.
Jassem; et al., "The Molecular and Cellular Basis of Reperfusion Injury Following Organ Transplantation.", Transplantation Reviews (1998), 12:14-33.
Kalimaris; et al., "Iron chelation prevents lung injury after major heptatectomy.", Hepatology Research (2010), 40:841-50.
Perrot et al., "Ischemia-Reperfusion-induced Lung Injury", American Journal of Respiratory and Critical Care Medicine, Feb. 3, 2003, pp. 490-511, vol. 167, Issue 4, American Thoracic Society, New York, NY.

(Continued)

*Primary Examiner* — Devang K Thakor
(74) *Attorney, Agent, or Firm* — Pamela J. Sherwood; Bozicevic, Field & Francis LLP

(57) ABSTRACT

Formulations and methods are provided for improving the function, i.e. clinical outcome, of solid organ transplants. Lung transplantation is of particular interest. In the methods of the invention, a nanoparticle formulation comprising an effective dose of an iron chelator active agent in nanoparticle form, including without limitation, deferoxamine (DFO), deferasirox (DFX), and deferiprone (DFP), etc. suspended in a carrier compatible with the tissue of interest, is topically applied to the surface of tissues at the site of anastomosis. The nanoparticles are comprised of the active agent and a pharmaceutically acceptable stabilizer.

7 Claims, 10 Drawing Sheets

(56) References Cited

OTHER PUBLICATIONS

Melillo et al., "Functional Requirement of the Hypoxia-responsive Element in the Activation of the Inducible Nitric Oxide Synthase Promoter by the Iron Chelator Desferrioxamine", Journal of Biological Chemistry, May 2, 1997, pp. 12236-12243, vol. 272, No. 18, ASBMB, Bethesda, MD.
Google NPL Search (2 pages); downloaded Aug. 17, 2016.
Sci Finder NPL 1 and NPL 2 results; downloaded Aug. 17, 2016.

* cited by examiner

HIF-1 MODULATOR PAINT FORMULATION AND USES THEREOF

GOVERNMENT RIGHTS

This invention was made with Government support under contracts HL082662 and TR000094 awarded by the National Institutes of Health. The Government has certain rights in this invention.

BACKGROUND

Lung transplantation is the definitive therapy for many end-stage pulmonary diseases and in many cases it is the only therapeutic option, despite having the highest mortality among all solid organ transplants. The fragility and the poor tolerance against ischemia of this organ is responsible for the fact that only 20% of the candidate lungs are currently being transplanted. The success of lung transplantation is limited by acute organ failure as well as chronic rejection against the transplant. Despite the improvement of surgical techniques and the development of better immunosuppressive drugs, short term airway complications taking place at the bronchial anastomosis (where the transplanted airways are surgically connected to the recipient' airways) continue to be a source of morbidity and mortality in those patients. Immediate ischemia of the donor bronchus and sacrifice of bronchial circulation during the surgical procedure have been recognized as the major risk factor for the development of airway complications.

The lung is unique among solid organ transplants in that it is not routinely reattached to the systemic circulation by bronchial arterial revascularization at the time of surgery. Blood supply to the airways in lung transplant recipients is therefore compromised with what blood flow is actually present presumably being provided by the deoxygenated pulmonary artery circulation. Therefore, from the onset, lung transplant airways have an impaired microcirculation due to the lack of a blood supply from the bronchial artery circulation, which results in relative airway tissue hypoxia. It has been previously demonstrated that the lack of bronchial arterial circulation in a lung transplant predisposes the transplanted airway to significant ischemia and hypoxia. It has also been shown that infectious agents can reside in the ischemic area, which includes the bronchial anastomosis of the transplant. Infection is one of the major causes of abnormal healing of the anastomosis as well as increased rate of acute rejection.

Several animal models, including the orthotopic tracheal transplant (OTT), heterotopic tracheal transplant, and orthotopic lung transplant models, have been used to study the pathology associated with human lung transplantation. The mouse OTT model has been shown to faithfully replicate the lymphocytic bronchitis seen following lung transplantation. The surgical anastomosis in the OTT model is similar to clinical transplantation in that it involves an end-to-end joining of donor with recipient airways. OTTs are therefore suitable for studying phenomena associated with clinical airway complications. It was previously shown that the airway microvascular circulation can be easily studied with the mouse OTT model and that the perfusion of the airway allograft can be used to assess the regeneration of the injured airway microvasculature, particularly at the anastomosis. The airway allograft is a free tissue, and there is no vascular perfusion prior to the formation of the microvascular anastomosis between the graft donor and the recipient. Therefore, earlier appearance of graft perfusion indicates an accelerated vascular anastomosis formation. Moreover, the OTT model is an ideal system to study airway microvascular repair and remodeling that occurs during alloimmune injury because of the well-organized planar anatomy of airway microvasculature. Using an OTT model, it was previously found that enhanced expression levels of hypoxia-inducible factor-1α (HIF-1α), the most important regulatory gene for hypoxic tissues, in airway grafts (by adenovirus-mediated gene therapy) promotes the recruitment of angiogenic cells, and prolongs tissue perfusion. It has also been shown that increased HIF-1α in the recipient cells promotes airway vascular anastomosis formation.

Ischemia is the principal factor that stimulates neovascularization, which is primarily regulated by HIF-1; this transcription factor consists of a constitutively expressed HIF-1β subunit and an oxygen-regulated HIF-1α subunit. In the presence of oxygen, two proline residues of HIF-1α are hydroxylated by the prolyl hydroxylase PHD2, facilitating von Hippel-Lindau tumor suppressor gene product (VHL) complex binding and HIF-1α degradation. In hypoxic conditions, PHD2 is inactive and HIF-1α is stabilized. HIF-1α then dimerizes with the β subunit, translocates to the nucleus, and induces gene transcription through binding to hypoxia response elements (HRE) of the oxygen-sensitive genes. HIF-1-mediated transcriptional responses orchestrate the expression of proangiogenic growth factors that facilitate angiogenesis by directly activating resident endothelial cells as well as recruiting circulating angiogenic cells.

Deferoxamine (DFO), deferasirox (DFX), and deferiprone (DFP) are all FDA-approved drugs for the treatment of iron overload conditions. DFO is a bacterial siderophore (N-[5-[[4-[5-[acetyl(hydroxy)amino]pentylamino]-4-oxobutanoyl]-hydroxyamino]pentyl]-N'-(5-aminopentyl)-N'-hydroxybutanediamide), DFX is a synthetic oral iron chelator (4-[(3Z,5E)-3,5-bis(6-oxocyclohexa-2,4-dien-1-ylidene)-1,2,4-triazolidin-1-yl]benzoic acid), DFP is an oral iron chelator (1,2-dimethyl-3-hydroxypyrid-4-one).

DFO, DFX and DFP have been extensively studied in various disease models. DFO can induce the transcriptional activity of HIF-1α in tumors. DFO stabilizes HIF-1α from degradation by inhibiting the activity of the PHDs through depletion of $Fe^{2+}$. Both DFO and DFX were shown to promote β cell function through upregulation of HIF-1α. In a rat median nerve injury model, local administration of DFO-loaded lipid particle promoted end-to-end nerve reconstruction. Through stabilizing HIF-1α protein, DFO has recently been shown to potentiate the homing of mesenchymal stem cells to promote target tissue regeneration. In a mouse hind limb ischemia model, DFO was shown to promote vascular repair and relief tissue ischemia.

Drug-loaded nanoparticles have emerged as a promising strategy for efficient drug delivery for the treatment of a variety of diseases. Drugs encapsulated in nanoparticles may display increased availability due to higher specific surface area and biocompatibility of the formulated particles.

As the size of a particle decreases, the surface area to the volume ratio increases, leading to an increased dissolution velocity, as described by Noyes-Whitney equation. Additionally, the saturation solubility of a particle increases as the particle size decreases, as described by the Kelvin and Ostwald-Freundlich equation, particularly after the particle size falls below about 1 µm. These phenomena make a nanoparticle formulation a highly effective means to enhance mass transfer from the particle to the surrounding medium. By suspending a drug as nanoparticles, one can achieve a dose that is higher than that of a solution, which is thermodynamically limited by the aqueous solubility of drug.

There is a great clinical interest in formulations and methods to improve the success of solid organ transplants, particularly lung transplants. Current surgical procedure of lung transplantation and post-operative management cannot effectively prevent airway ischemia and associated airway complications. The present invention addresses the need to limit airway complications.

PUBLICATIONS

Jiang et al. (2011) *J Clin Invest.* 121(6):2336-2349 discusses adenovirus-mediated HIF-1α gene transfer to promote repair of mouse airway allograft microvasculature and attenuation of chronic rejection. Also see commentary by Wilkes (2011) *J Clin Invest.* 121(6):2155-2157. Jiang et al. (2013) *Journal of Molecular Medicine* (in press), describes upregulation of HIF-1α gene in recipient cells through genetically knocking down of VHL promotes airway perfusion and prevents fungus invasion.

SUMMARY OF THE INVENTION

Formulations and methods are provided for improving the function, i.e. clinical outcome, of a lung transplant. In certain embodiments, formulations of the invention comprise nanoparticles of an effective dose of HIF-1α stabilizer suspended in a carrier compatible with the tissue of interest. The formulation is topically applied to the surface of tissues at the site of anastomosis, usually immediately prior to, or at the time of transplantation surgery.

In one embodiment, a HIF-1α stabilizer is an iron chelator such as, deferoxamine (DFO), deferasirox (DFX), and deferiprone (DFP). In other embodiments, the iron chelator is selected from the group consisting of PIH (pyridoxal isonicotinoyl hydrozone), DFT (a desferrithiocin), DBED (N,N'-bis-dibenzyl ethylenediaminediacetic acid), FDO (a furildioxime), BDP (dexrazoxane), ZIL (Zileuton), DOX (doxorubicin), BHT (a bis-hydroxylaminetriazine), HBP (a 3-hydroxybezopyran-4-one), CAC (enterobactin), Triapine and ciclopirox, Lactoferrin, DP44mT, clioquinol, sideromycines, Salicylaldehyde isonicotinoyl hydrazine, S956711, FG-0041, TM6008, and analogs of any of the foregoing with iron chelating activity.

In another embodiment, HIF-1α stabilizer is a non-iron-chelating PHD inhibitor. In various embodiments, the PHD inhibitor is selected from a group consisting of TM6089, FG-4592, FG-2216, JNJ42041935, FG-4497, EDHB (ethyl-3,4-dihydroxybenzoate), DMOG (dimethyloxallyl glycine), N-OG (N-oxalyglycine), DHB (3,4-dihydroxybenzoate), IOX2 (Axon1921), IOX1, Axon1948, 2,4-DPD, GSK360A, FG-6515, 1,4-DPCA (4,4α-dihydro-4-oxo-1,10-phenanthroline-3-carboxylic acid), ICA ((PHD-I) 2-(1-chloro-4-hydroxyisoquinoline-3-carboxamido)acetate), and analogs of any of the forgoing with non-iron-chelating PHD inhibiting activity.

In preferred embodiments the HIF-1α stabilizer is formulated as encapsulated nanoparticles. A nanoparticle formulation provides the advantages of delivery over an extended period of time; and targeted to the interior of cells to stabilize HIF-1α. Encapsulation improves the sustained release. Suspension of the nanoparticles in a lipid formulation improves the penetration of the drug into tissues and cells.

In some embodiments of the invention, the solid organ is a lung. The present invention provides a system for limiting airway complications by alleviation of airway tissue ischemia and hypoxia, and overcoming rejection of a transplanted lung by maintaining open small airways. In such embodiments, the nanoparticles may comprise active agent admixed with a stabilizer that is compatible with tracheal contact. The formulation is topically applied, by direct contact with at least one inner or outer surface involved in anastomosis of a lung, including the site of tracheal anastomosis, which may include at least one bronchial surface. For example, the trachea, bronchia, etc. may be soaked or administered with the pharmaceutical formulation, where the formulation is contacted with the tissue for a period of time sufficient to allow penetration of the active agent, for example to a depth of at least about 1 mm, at least about 1.5 mm, at least about 2 mm, etc., which period of time may be at least 1 minute, at least 5 minutes, at least 10 minutes, or more.

In some embodiments, a lung being transplanted is maintained in functional condition by the methods of the invention, i.e. by contacting at least one tracheal surface with an effective dose of a nanoparticle formulation of the invention. In such embodiments, ischemia within the transplanted lungs is avoided by maintenance of the patency of the small airways of the lung. The methods of the invention also provide for an increase in the percentage of successful transplanted lungs. The benefit of methods of the invention can include: 1) promoting the healing of the bronchial anastomosis, 2) increasing airway perfusion and relief of hypoxia, 3) decreasing acute organ failure, 4) prevention or delay of chronic rejection. All of these benefits are related to the fact that preservation of airway perfusion limits the fibrotic airway remodeling that accompanies rejection responses and also limits the invasiveness of pathogens.

An effective dose of active agent is that dose which, when provided to a patient, is effective in improving microvascular anastomosis formation and microvascular perfusion at the transplanted organ, for example in improving airway microvascular perfusion after a period of from about 3 to about 10 days, relative to a control transplant in the absence of treatment with the methods of the invention. An effective dose may vary depending on the active agent and the size of the surface that is being treated. In some embodiments, e.g. using DFO as an active agent, the effective dose for administration at the time of transplantation surgery may be at least about 10 mg, at least about 50 mg, and not more than about 1000 mg, usually not more than about 500 mg, or not more than about 200 mg, and may be from about 100 mg to about 500 mg.

In some embodiments a composition is provided for topical administration to an internal organ, particularly during transplantation, where the composition comprises or consists essentially of an effective dose of an iron chelator active agent in nanoparticle form, including without limitation, deferoxamine (DFO), deferasirox (DFX), and deferiprone (DFP), etc. suspended in a carrier compatible with the tissue of interest. In other embodiments, the iron chelator is selected from the group consisting of PIH (pyridoxal isonicotinoyl hydrozone), DFT (a desferrithiocin), DBED, FDO (a furildioxime), BDP (dexrazoxane), ZIL (Zileuton), DOX (doxorubicin), BHT (a bis-hydroxylaminetriazine), HBP (a 3-hydroxybezopyran-4-one), CAC (enterobactin), Triapine and ciclopirox, Lactoferrin, DP44mT, clioquinol, sideromycines, Salicylaldehyde isonicotinoyl hydrazine, S956711, FG-0041, TM6008, and analogs of any of the foregoing with iron chelating activity. In other embodiments the nanoparticles are comprised of a non-iron-chelating PHD inhibitor, which may be selected from a group consisting of TM6089, FG-4592, FG-2216, JNJ42041935, FG-4497, EDHB, DMOG, N-OG, DHB (3,4-dihydroxybenzoate), IOX2 (Axon1921), IOX1, Axon1948, 2,4-DPD, GSK360A, FG-6515, 1,4-DPCA, ICA, and analogs of any of the forgoing with non-iron-chelating PHD inhibiting activity.

The nanoparticles are usually comprised of the active agent and a pharmaceutically acceptable stabilizer, where the active agent may be at least about 5% of the total nanoparticle weight, and not more than about 50% of the total nanoparticle weight. The nanoparticles may be suspended in a pharmaceutically acceptable carrier at a concentration that provides for the desired dose of active agent.

Another aspect of the present invention relates to the use of an effective dose of an iron chelator active agent in nanoparticle form in the manufacture of a medicament for improving the function of a solid organ transplant, wherein the medicament is topically applied to the surface of tissues at the site of anastomosis, usually immediately prior to, or at the time of transplantation surgery.

The pharmaceutical formulation of the invention may be packaged for use during surgery, in a sterile unit dose, optionally with applicator, and may include labeling and/or instructions for use.

DETAILED DESCRIPTION OF THE EMBODIMENTS

Figure 1:
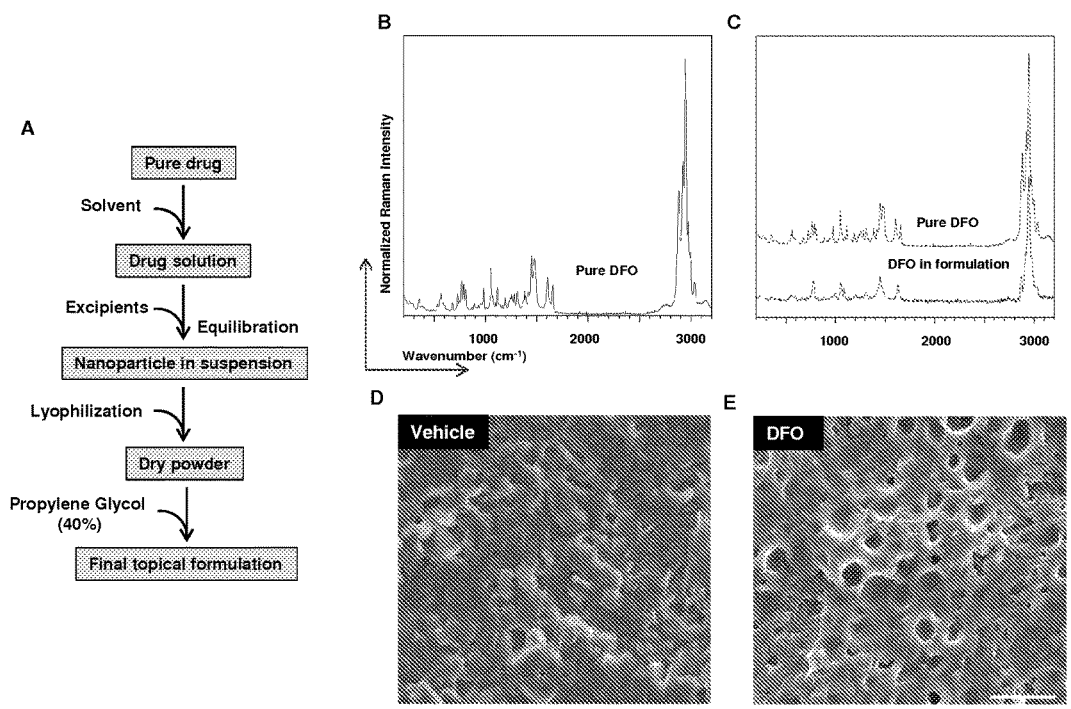
FIG. 1. Analysis of drug molecule structure and morphology study of encapsulated nanoparticles. A. A schematic showing the procedure for nanoparticle formulation. B and C. Drug structure analysis by Raman spectroscopy showing the structures of pure DFO (B) and DFO in the nanoparticle formulation (C). D and E. Nanoparticle morphology analysis shows that the vehicle (D) and DFO dry powders (E) are homogeneous. Scale bar: 20 µm (D, E).

The clinical outcome of a solid organ transplantation, including without limitation lung transplantation, is improved by directly contacting the surface of tissues at the site of anastomosis, usually immediately prior to, or at the time of transplantation surgery, with a nanoparticle formulation comprising an effective dose of an iron chelator active agent in nanoparticle form, including without limitation, deferoxamine (DFO), deferasirox (DFX), and deferiprone (DFP), etc. suspended in a carrier compatible with the tissue of interest.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a nanoparticle" includes a plurality of such nanoparticles and equivalents thereof known to those skilled in the art, and so forth.

Definitions

The terms "treating", and "treatment" and the like are used herein to generally mean obtaining a desired pharmacological and/or physiological effect. The effect may be prophylactic in terms of preventing or partially preventing a disease, symptom or condition thereof and/or may be therapeutic in terms of a partial or complete cure of a condition, symptom or adverse effect attributed to the condition. The term "treatment" as used herein covers particularly the topical application of a composition comprising an iron chelator active agent in nanoparticle form at the site of trachea anastomosis. The term "prophylaxis" is used herein to refer to a measure or measures taken for the prevention or partial prevention of a disease or condition.

The term "subject" includes mammals, e.g. cats, dogs, horses, pigs, cows, sheep, rodents, rabbits, squirrels, bears, primates such as chimpanzees, gorillas, and humans.

As used herein, the term "solid organ transplantation" is used in accordance with the conventional meaning of the term, where an organ from a donor, which donor may be living or deceased, in placed into the body of a recipient in the appropriate position and cardiovascular connections to be physiologically integrated into the recipient. Transplantation of lung(s) is of particular interest for the methods of the invention, although the methods do not exclude transplantation of other organs, e.g. pancreas and including kidney, pancreatic islet cells; heart; intestine, liver; skin, and the like as known in the art. In some embodiments the transplantation involves multiple anastomoses, e.g. transplantation of lung, heart, liver, kidney. The transplanted organ may be referenced as a "graft", and the physiological integration of the organ may be referred to as engraftment.

The term "graft management" refers to therapeutic methods that induce and/or promote repair engraftment of a solid organ, but not limited to, lung transplantation.

As used herein, the term "iron chelating compound" or "iron chelator" is intended to mean a compound that binds iron between one or more binding sites so as to form a chelate. An iron chelating compound bound or complexed with iron is referred to herein as an iron chelator. Chelators may be categorized by their binding structures. Deferiprone (DFP) is a bidentate chelator requiring three molecules each with two iron binding sites for the six coordination sites of iron(III). Deferasirox (DFX), a tridentate chelator, requires two molecules for iron(III) coordination, and desferrioxamine (DFO) is a hexadentate chelator binding iron in a 1:1 ratio.

Iron chelating compounds useful in the methods and formulations of the invention include chelation compounds that can bind to all oxidation states of iron including, for example, iron (–II) state, iron (–I) state, iron (0) state, iron (I) state, iron (II) state (ferrous), iron (III) state (ferric), iron (IV) state (ferryl) and/or iron (V). Iron chelation therapy refers to the use of an iron chelator to bind with iron in vivo to form an iron chelate so that the iron loses its toxic effect or adverse physiological activity.

An iron chelating compound useful in a composition of the invention can include any chelator or other molecule that can bind and prevent iron utilization. Specific examples of iron chelating compounds included in the compositions of the invention include, for example, deferoxamine, deferiprone and deferasirox. These exemplary iron chelating compounds are particularly useful because they have been approved in various countries for therapeutic indications and are therefore, well characterized, safe and non-toxic in humans.

The term "deferoxamine" (also known as desferrioxamine B, desferoxamine B, DFO-B, DFOA, DFB, DFO or desferal) is a bacterial siderophore produced by the actinobacteria *Streptomyces pilosus*, having the structure (N-[5-[[4-[5-[acetyl(hydroxy)amino]pentylamino]-4-oxobutanoyl]-hydroxyamino]pentyl]-N'-(5-aminopentyl)-N'-hydroxybutanediamide). It has medical applications including, for example, as a chelating agent to remove excess iron from the body. The mesylate salt of DFO-B is commercially available.

The term "deferiprone," as it is used herein is intended to mean an iron chelating compound having the structure 1,2 dimethyl-3-hydroxypyrid-4-1. Deferiprone (DFP), also is known in the art as L1, CP20, Ferriprox, or Kelfer. Deferiprone, is a member of the α-ketohydroxypyridine class of iron chelators and is commercially available from, for example, Apotex, Inc. (Weston, Ontario, Canada).

The term "deferasirox" as it is used herein is intended to mean an iron chelating compound having the structure 4-[3,5-Bis(2-hydroxyphenyl)-1H-1,2,4-triazol-1-yl]-benzoic acid and having a molecular weight of 373.4 daltons. Deferasirox, also is known in the art as DFX, Exjade® or ICL 670, is a member of the class of tridentate iron chelators referred to as N-substituted bis-hydroxyphenyl-triazoles. Deferasirox is commercially available from, for example, Novartis, Corp. (Basel, Switzerland), for example, under the trademark Exjade®. According to the present invention, the terms "deferasirox", "ICL670", "Exjade®" are meant to refer to the active ingredient 4-[3,5-Bis(2-hydroxyphenyl)-1H-1,2,4-triazol-1-yl]-benzoic acid, e.g. 4-[3,5-Bis(2-hydroxyphenyl)-1H-1,2,4-triazol-1-yl]-benzoic acid or a pharmaceutically acceptable salt thereof. Deferasirox, its process of manufacture and its uses are described in, for example, U.S. Pat. Nos. 6,465,504B1 and 6,595,750 B2, and in European Patent No. EP0914118. Pharmaceutical preparations comprising 4-[3,5-Bis(2-hydroxyphenyl)-1H-1,2,4-triazol-1-yl]-benzoic acid or a pharmaceutically acceptable salt thereof are described in, for example, International Patent Application WO2004/035026.

Other iron chelating compounds also can be included in the compositions of the invention. Such other iron chelating compounds are well known in the art and include, for example, naturally occurring siderophores and xenosiderophores as well and non-naturally occurring compounds such as deferiprone and deferasirox.

Non-naturally occurring iron chelating compounds are exemplified by members of the hydroxypyridin-4-one (HPO) class of chelators, such as deferiprone, members of the N-substituted bis-hydroxyphenyl-triazole class of chelators such as deferasirox, diethylenetriaminepentaacetic acid (DTPA) and deferoxamine. Deferiprone, deferasirox and any of the above exemplary iron chelating compounds as well as others well known in the art can be included in the iron chelating compound containing compositions of the invention.

Siderophores and xenosiderophores include, for example, hydroxamates and polycarboxylates. The hydroxamates contain an N-δ-hydroxyornithine moiety and are generally categorized into four exemplary families. One category includes rhodotorulic acid, which is the diketopiperazine of N-δ-acetyl-L-N δ-hydroxyornithine. Included within this category are derivatives such as dihydroxamate named dimerum acid. A second category includes the coprogens, which contain an N-δ-acyl-N-δ-hydroxy-L-ornithine moiety. Coprogens also can be considered trihydroxamate derivatives of rhodotorulic acid with a linear structure. A third category includes the ferrichromes, which consist of cyclic peptides containing a tripeptide of N-δ-acyl-N-δ-hydroxyornithine and combinations of glycine, serine or alanine. The fourth exemplary category includes the fusarinines, also called fusigens, which can be either linear or cyclic hydroxamates. Fusarinine is a compound characterized by N acylation of N-hydroxyornithine by anhydromevalonic acid.

The polycarboxylates consist of a citric acid-containing polycarboxylate called rhizoferrin. The molecule contains two citric acid units linked to diaminobutane. Rhizoferrin is widely distributed among the members of the phylum Zygomycota, having been observed in the order Mucorales and in the order Entomophthorales. Other categories of siderophores useful as iron chelating compounds in the compositions of the invention include, for example, the phenolate-catecholate class of siderophores, hernin, and β-ketoaldehyde phytotoxins.

The amount of iron chelating compound included in a composition of the invention can vary but will generally be a therapeutically effective amount or an amount that can be reconstituted or diluted to a therapeutically effective amount. For example, effective amounts of iron chelating compounds of the invention are described further below with reference to the methods of the invention. An amount of one, some or all iron chelating compounds can be formulated in a composition of the invention to correspond to these exemplary effective amounts.

An iron chelating compound also can be formulated in a composition of the invention in amounts greater than a therapeutically effective amount for either short or long-term storage and the end user can dilute the formulation prior to use to a desired therapeutically effective amount. Alternatively, an iron chelating compound included in a composition of the invention can be lyophilized or produced in powder or other solid form and the end user can reconstitute the dry formulation prior to use to a desired therapeutically effective amount.

In some embodiments, the iron chelating agent is a HIF-1α potentiating agent, or alternatively a HIF-1a potentiating agent other than an iron chelator. HIF-1 is an oxygen-dependent transcriptional activator, which plays crucial roles in the angiogenesis of tumors and mammalian development. HIF-1 consists of a constitutively expressed HIF-1β subunit and one of three subunits (HIF-1α, HIF-2α or HIF-3α). The stability and activity of HIF-1α are regulated by various post-translational modifications, hydroxylation, acetylation, and phosphorylation. Under normoxia, the HIF-1α subunit is rapidly degraded via the vHL-mediated ubiquitin-proteasome pathway. The association of vHL and HIF-1α under normoxic conditions is triggered by the hydroxylation of prolines and the acetylation of lysine within a polypeptide segment known as the oxygen-dependent degradation (ODD) domain. During hypoxic conditions HIF-1α subunit becomes stable and interacts with coactivators such as p300/CBP to modulate its transcriptional activity.

HIF-1 acts as a master regulator of numerous hypoxia-inducible genes under hypoxic conditions. The heterodimer HIF-1 binds to the hypoxic response elements (HREs) of target gene regulatory sequences, resulting in the transcription of genes implicated in the control of cell proliferation/survival, glucose/iron metabolism and angiogenesis, as well as apoptosis and cellular stress. Some of these direct target genes include glucose transporters, the glycolytic enzymes, erythropoietin, and angiogenic factor vascular endothelial growth factor (VEGF).

The term "HIF-1", as used herein, includes both the heterodimer complex and the subunits thereof, HIF-1α and HIF-1. The HIF 1 heterodimer consists of two helix-loop-helix proteins; these are termed HIF-1α, which is the oxygen-responsive component (see, e.g., Genbank accession no. Q16665), and HIF-1β. The latter is also known as the aryl hydrocarbon receptor nuclear translocator (ARNT).

HIF-1α potentiating agents include agents that increase the accumulation of, or stability of, HIF-1α; directly provide HIF-1α activity; or increase expression of HIF-1. Such agents are known in the art, or may be identified through art-recognized screening methods.

Compounds currently identified as HIF-1 potentiating agents include cofactor-based inhibitors such as 2-oxoglutarate analogues, ascorbic acid analogues and iron chelators such as desferrioxamine (DFO), the hypoxia mimetic cobalt chloride ($CoCl_2$), and mimosine, 3-Hydroxy-4-oxo-1(4H)-pyridinealanine, or other factors that may mimic hypoxia. Also of interest are hydroxylase inhibitors, including deferiprone, 2,2'-dipyridyl, ciclopirox, dimethyloxallyl glycine (DMOG), L-Mimosine (Mim) and 3-Hydroxy-1,2-dimethyl-4(1H)-Pyridone (OH-pyridone). Other HIF hydroxylase inhibitors are described herein, including but not limited to, oxoglutarates, heterocyclic carboxamides, phenanthrolines, hydroxamates, and heterocyclic carbonyl glycines (including, but not limited to, pyridine carboxamides, quinoline carboxamides, isoquinoline carboxamides, cinnoline carboxamides, beta-carboline carboxamides, including substituted quinoline-2-carboxamides and esters thereof; substituted isoquinoline-3-carboxamides and N-substituted arylsulfonylamino hydroxamic acids (see, e.g., PCT Application No. WO 05/007192, WO 03/049686 and WO 03/053997), and the like.

Compounds reported to stabilize HIF-1α also include [(3-hydroxy-6-isopropoxy-quinoline-2-carbonyl)-amino]-acetic acid, [3-hydroxy-pyridine-2-carbonyl)-amino]-acetic acid, [N-((1-chloro-4-hydroxy-isoquinoline-3-carbonyl)-amino)-acetic acid, [(7-bromo-4-hydroxy-isoquinoline-3-carbonyl)-amino]-acetic acid, [(7-chloro-3-hydroxy-quinoline-2-carbonyl)-amino]-acetic acid, [(1-bromo-4-hydroxy-7-kifluoromethyl-isoquinoline-3-carbonyl)-amino]-acetic acid, [(1-Bromo-4-hydroxy-7-phenoxy-isoquinoline-3-carbonyl)-amino]-ace-tic acid, [(1-Chloro-4-hydroxy-7-phenoxy-isoquinoline-3-carbonyl)-amino]-acetic acid, [(1-Chloro-4-hydroxy-7-methoxy-isoquinoline-3-carbonyl)-amino]-acetic acid, [(1-chloro-4-hydroxy-isoquinoline-3-carbonyl)-amino]-acetic acid, [(4-Hydroxy-7-phenoxyisoquinoline-3-carbonyl)-amino]-acetic acid, [(4-Hydroxy-7-phenylsulfanyl isoquinoline-3-carbonyl)-amino]-acetic acid, [(4-Hydroxy-6-phenylsulfanyl-isoquinoline-3-carbonyl)-amino]-acetic acid, 4-Oxo-1,4-dihydro-[1,10]phenanthroline-3-carboxylic acid, 4-hydroxy-5-methoxy-[1,10] phenanthroline-3-carboxylic acid ethyl ester, [(7-benzyloxy-1-chloro-4-hydroxy-isoquinoline-3-carbonyl)-amino]-acetic acid methyl ester, and 3-{[4-(3,3-Dibenzyl-ureido)-benzenesulfonyl]-[2-(4-methoxy-phenyl)-ethyl]-amino}-N-hydroxy-propionamide.

The term "pharmaceutically acceptable" as used herein refers to a compound or combination of compounds that will not impair the physiology of the recipient human or animal to the extent that the viability of the recipient is compromised. Preferably, the administered compound or combination of compounds will elicit, at most, a temporary detrimental effect on the health of the recipient human or animal.

The formulations of the invention can comprise nanoparticles of an iron chelating active agent, or a non-chelating HIF-1α stabilizing agent as described above, and generally admixed with a stabilizer or cocktail of stabilizers. The nanoparticle can comprise or consist essentially of the active agent at a concentration of up to about 5%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75% of the total weight, and the like. It will be understood by one of skill in the art that two or more active compounds can be co-formulated, in which case the purity shall refer to the combined active agents.

In some embodiments the nanoparticle comprises from about 40% to about 60% by weight active agent, and may comprise from about 45% to about 50% by weight active agent.

The balance of the nanoparticle weight is provided by stabilizer, i.e. up to about 95%, up to about 90%, up to about 85%, up to about 80%, up to about 75%, up to about 70%, up to about 65%, up to about 60%, up to about 55%, up to about 50%, up to about 45%, up to about 40% of the total weight.

In some embodiments the nanoparticle comprises from about 40% to about 60% by weight stabilizer, and may comprise from about 50% to about 55% by weight stabilizer or combination of stabilizers.

The nanoparticles have a controlled size, as appropriate for optimization of drug delivery. Usually the particle will have a diameter of up to about 10 nm, up to about 50 nm, up to about 100 nm, up to about 250 nm, up to about 500 nm, up to about 1 µm, up to about 2.5 µm, up to about 5 µm, and not more than about 10 µm in diameter. In some embodiments the nanoparticle size is from about 100 nm to about 5 µm in diameter, for example from about 100 nm to about 500 nm, from about 500 nm to about 1 µm, and the like. The nanoparticle optionally has a defined size range, which may be substantially homogeneous, where the variability may not be more than 100%, 50%, or 10% of the diameter.

Nanoparticles can be formed by various methods, including, in some embodiments, the methods exemplified herein. Methods of interest may include, without limitation, particles precipitated out of solution (bottom-up) for example by lyophilization, or milled from larger particles (top-down). In both mechanisms, the total surface area increases which increases the free energy of the particles. The system compensates for this increase in free energy by dissolving crystalline nuclei and precipitating onto other particles in a process known as Ostwald Ripening or by agglomerating smaller particles. Some processes that are currently under investigation include: wet milling, supercritical fluid extraction, spray drying; electrospray; high-pressure homogenization; and recrystallization via solvent displacement. In addition to chemical processing technologies, multiple studies have examined different polymeric nanoparticle fabrication methods. These techniques generally involve polyelectrolyte complex formation, double emulsion/solvent evaporation techniques, or emulsion polymerization techniques. Spray drying is a process that uses jets of dissolved or suspended drug in an aqueous or other fluid phase that is forced through high pressure nozzles to produce a fine mist. Often, a bulking agent will be added to the fluid as well. The aqueous or other liquid contents of the mist evaporate, leaving behind a fine powder. A modification of spray drying, called air nebulization spray drying, uses two wedge-shaped nozzles through which compressed air passes and liquid solutions pass at high velocity. The wedge-shaped nozzle acts as a fluid acceleration zone where the four streams collide at high velocity, producing a shock wave that generates fine droplets. The droplets then descend into a column while being dried into a solid powder by heated air before being collected.

Stabilizers of interest include, without limitation, lecithin, which are naturally occurring mixtures of diglycerides of stearic, palmitic, and oleic acids, linked to the choline ester of phosphoric acid. Lecithin may be added to the first mixture, with the drug and oil. Other stabilizers of interest include, for example, cationic lipids, particularly phospholipids. A protein, such as albumin (for example bovine serum albumin, human serum albumin, etc.) may be used. Polyvinylpyrrolidone (PVP) is a water soluble branched polymer of N-vinylpyrrolidone, having a molecular weight of about 10K, and may be higher, e.g. from about 20K to 50K. Chitosan is a linear polysaccharide composed of randomly distributed β-(1,4) D-glucosamine and N-acetyl-D-glucosamine.

In some embodiments, the nanoparticles are stabilized with a mixture of albumin or other suitable protein, and a cationic lipid, e.g. in a ratio of about 1:15, 1:12, 1:11, 1:10; 1:9; 1:8, 1:5, etc. by weight. During formation of the nanoparticles, the stabilizer of the nanoparticles may be added to a suspension of the active agent before lyophilization.

The term "cationic lipids" is intended to encompass molecules that are positively charged at physiological pH, and more particularly, constitutively positively charged molecules, comprising, for example, a quaternary ammonium salt moiety. Cationic lipids used in the methods of the invention typically consist of a hydrophilic polar head group and lipophilic aliphatic chains. See, for example, Farhood et al. (1992) *Biochim. Biophys. Acta* 1111:239-246; Vigneron et al. (1996) *Proc. Natl. Acad. Sci.* (USA) 93:9682-9686.

Cationic lipids of interest include, for example, imidazolinium derivatives (WO 95/14380), guanidine derivatives (WO 95/14381), phosphatidyl choline derivatives (WO 95/35301), and piperazine derivatives (WO 95/14651). Examples of cationic lipids that may be used in the present invention include 1,2-distearoyl-sn-glycero-3-phosphocholine (DSPC); 1,2-dipalmitoyl-sn-glycero-3-phosphocholine (DPPC); DOTIM (also called BODAI) (Solodin et al., (1995) Biochem. 34: 13537-13544), DDAB (Rose et al., (1991) BioTechniques 10(4):520-525), DOTMA (U.S. Pat. No. 5,550,289), DOTAP (Eibl and Wooley (1979) Biophys. Chem. 10:261-271), DMRIE (Feigner et al., (1994) J. Biol. Chem. 269(4): 2550-2561), EDMPC (commercially available from Avanti Polar Lipids, Alabaster, Ala.), DCChol (Gau and Huang (1991) Biochem. Biophys. Res. Comm. 179:280-285), DOGS (Behr et al., (1989) Proc. Natl. Acad. Sci. USA, 86:6982-6986), MBOP (also called MeBOP) (WO 95/14651), and those described in WO 97/00241.

The term "carrier" as used herein refers to any pharmaceutically acceptable solvent or agent that will allow a therapeutic composition to be administered directly to a body surface, particularly for direct contact on the surface of tissues at the site of anastomosis, immediately prior to, or at the time of transplantation surgery. The carrier allows the active agent to be topically applied to an exposed surface of an organ for transplantation and the site of the recipient where the organ is to be placed. A preferred carrier provides for drug penetration to a depth of at least about 1 mm, at least about 1.5 mm, at least about 2 mm from the surface, e.g. over a period of up to about 5 minutes, up to about 10 minutes, up to about 15 minutes, up to about 30 minutes, etc.

Carrier as used herein, therefore, refers to such solvent as, but not limited to, water, oil, saline, oil-water emulsions, or any other solvent or combination of solvents and compounds known to one of skill in the art that is pharmaceutically and physiologically acceptable to the recipient human or animal.

The nanoparticles are suspended in the carrier at a concentration suitable for providing homogenous and effective drug application upon topical contact. In some embodiments the nanoparticles are provided as a dried powder with instructions for mixing. In other embodiments the nanoparticles and carrier are provided as separate entities, with instructions for mixing. In other embodiments the nanoparticles and carrier are formulated as a single entity, e.g. where the nanoparticles comprise up to about 5% weight/volume of the formulation, up to 7.5%, up to 10%, up to 12.5%, up to 15%, up to 17.5%, up to 20%, up to 22.5%, up to 25%, etc. In some such embodiments the nanoparticles comprise from about 5% to about 15%, or from about 7.5% to about 12.5% w/v of the formulation.

In some embodiments the carrier is propylene glycol or similar compound, e.g. glycerol, 1,3-butanediol, sorbitol, etc. provided in an aqueous solution. The carrier solution may comprise an aqueous solution of up to about 25% propylene glycol, glycerol, 1,3-butanediol, sorbitol, etc., up to about 30%, up to about 35%, up to about 40%, up to about 45%, up to about 50%, up to about 55%, up to about 60%, up to about 65%, up to about 70%, up to about 75%, etc. In some embodiments the carrier comprises an aqueous solution of propylene glycol or similar compound, e.g. glycerol, 1,3-butanediol, sorbitol, etc. at a concentration of from about 30% to about 50%, e.g. around about 40%.

In alternative embodiments the carrier is a physiologically acceptable oil. As used herein, the term refers to an oil, particularly a triglyceride, that can be applied to internal organs, particularly applied to lung tissue, including without limitation the trachea. Triglycerides are of particular interest for this purpose, which includes short, medium and long chain triglycerides. The term "trigylceride" as used herein refers to a triester of glycerol (HO—CH(CH$_2$OH)$_2$). The three ester groups may be identical, two of the three may be the same, with the third being different or all three may be different. The term "short chain triglyceride" as used herein, refers to a triglyceride comprising ester groups containing less than 8 linear carbon atoms. The term "medium chain triglyceride" as used herein, refers to a triglyceride comprising ester groups containing 8 to 12 linear carbon atoms. In some embodiments the oil is Labrafac™ Lipophile WL1349.

Surfactants of interest include both ionic, e.g. cationic, anionic and zwitterionic, and nonionic surfactants, particularly non-ionic. Specific surfactants and detergents of interest include: Cationic surfactants, such as polyquaternium-10, guar hydroxypropyltrimonium chloride, laurtrimonium chloride, cetrimonium chloride, laurtrimonium bromide, cetrimonium bromide, lauralkonium chloride, stearalkonium chloride, trimethylglycine, ditallowdimonium chloride, alkyl dimethyl benzylammonium chlorides and alkyl trimethylammonium methosulfate, Alkyltrimethylammonium Bromides, Cetyldimemylethylammonium Bromide, Benzalkonium Chloride, Cetylpyridinium Benzethonium Chloride, Decamethonium Bromide, Benzyldimethyldodecylammonium Bromide, Dimethyldioctadecylammonium Bromide, Benzyldimethylhexadecylammonium Bromide, Methylbenzethionium Chloride, Benzyldimethyltetradecylammonium Bromide, Methyltrioctylammonium Chloride, N,N\N'-Polyoxyethylene(10)-N-tallow-1,3-diaminopropane, and the like;

Anionic surfactants, such as naturally occurring anionic surfactant compounds or derivatives thereof, e.g. bile salts (cholic acid, dehydrocholic, deoxycholic, lithocholic, taurcholic acid, glycocholic acid, etc.,) as well as synthetic surfactants and detergents, e.g. sodium dodecyl sulfate, sodium lauroyl glutamate, sodium undecenyl glutamate, sodium cetyl glutamate, lauryl phosphate, cetyl phosphate, disodium laureth-3 sulfosuccinate, sodium cocoyl isethionate, sodium lauryl sulfate, sodium tetradecyl sulfate, sodium 2-ethylhexyl sulfate, sodium octylphenol glycolether sulfate, sodium dodecylbenzene sulfonate, sodium lauryldiglycol sulfate, ammonium tritertiarybutyl phenol and penta- and octa-glycol sulfonates, disodium n-octyldecyl sulfosuccinate, sodium dioctyl sulfosuccinate, sodium diisooctyl sulphosuccinate, acyl isethionates, acyl taurates, fatty acid amides of methyl tauride and acyl sarcosinates, Aerosol 22, Dioctyl Sulfosuccinate, Dodecyl Sulfate, Aerosof-OT, 1-Dodecansulfonic Acid, 1-Nonanesulfonic Acid, Alginic Acid, Glycocholic Acid, 1-Octanesulfonic Acid, Caprylic Acid, Glycodeoxycholic Acid, 1-Pentanesulfonic Acid, 1-Decanesulfonic Acid, 1-Heptanesulfonic Acid, Taurocholic Acid, Dehydrocholic Acid, 1-Hexanesulfonic Acid, Taurodeoxycholic Acid, Deoxycholic Acid, N-Lauroylsarcosine, Tergitoland the like;

Zwitterionic surfactants, e.g. CHAPS, lauramidopropyl betaine, cocamidopropyl betaine, cocamidopropyl hydroxysultaine, cocamidopropylamine oxide, lauryl betaine, lauryl hydroxysultaine, lauraminoxide, myristamine oxide, sodium lauroamphoacetate, sodium cocoamphoacetate and lauroamphocarboxyglycinate CHAPS$^+$, N-Octadecyl-N,N-dimethyl-3-ammonio-CHAPSO$^+$, 1-propmes fonateN-Decyl-N, N-dimemyl-3-ammomo-N-Octyl-N,N-dime yl-3-ammonio-I-propanesulfonate, I-propanesulfonateN-Dodecyl-N,N-dimethyl-3-ammonio-Phosphatidylcholine, 1-propanesulfonate B-Tetradecyl-N,N-dimethyl-3-ammonio-N-Hexadecyl-N,N-dimethyl-3-ammonio-1-propanesulfonate, 1-propanesulfonate and the like; and Non-ionic surfactants, e.g. nonoxynol-9, glycol monostearate, glycol distearate, PEG-150 distearate, methyl gluceth-10, methyl gluceth-20, methyl glucose sesquistearate, sodium PCA, polyethoxy 20 sorbitan monooleate, polyoxyethylene ethers and TRITON®, TERGITOL® and SURFYNOL™ surfactants, BIGCHAP, Decanoyl-N-methylglucamide, n-Nonyl α-D-glucopyranoside, n-Decyl-α-D-Glucopyranoside, n-Nonyl β-D-glucopyranoside, n-Decyl-β-D-Glupyranoside, Octanoyl-N-methylglucamide, n-Decyl-β-D-Maltopyranoside, n-Octyl α-D-Glucopyranoside, Deoxy-BIGCHAP, n-Octyl β-D-Glucopyranoside, n-Dodecyl-β-D-Glucopyranoside, Octyl β-D Thiogalactopyranoside, n-Dodecyl-α-D-Maltoside, Octyl β-D-Thioglucopyranoside, n-Dodecyl-β-D-Maltoside, Polyoxyethylene Esters, Heptanoyl-N-methylglucamide, Polyoxyethylene Ethers, n-Heptyl-β-D-Glucopyranoside, Polyoxyethylene-sorbital Esters, n-Heptyl-β-D-Thioglucopyranoside, Sorbitan Esters, n-Hexyl-β-Dglucopyranoside, n-Tetradecyl β-D-Maltoside, Igepal CA-630, Tritons, 1-Monooleoyl-rac-glycerol, Nonanoyl-N-methylgluamide, Tyloxapol, n-Undecyl β-D-Glucopyranoside, Saponin, Nonidet P-40, Digitonin, and the like; etc.

Of interest are poloxamers, which are nonionic triblock copolymers composed of a central hydrophobic chain of polyoxypropylene (poly(propylene oxide)) flanked by two hydrophilic chains of polyoxyethylene (poly(ethylene oxide)). Because the lengths of the polymer blocks can be customized, many different poloxamers exist that have slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). In some embodiments Poloxamer 188 is used.

Formulations of the Invention

The formulations of the invention provide nanoparticles having a high concentration of an iron chelating active agent, stabilized and in a carrier acceptable for topical contact, e.g. for contact with an airway surface. The formulation for administration is usually a suspension of the iron chelating active agent nanoparticles, e.g. DFO, DFX, DFP, and the like, suspended in a suitable carrier. In some embodiments the active agent is DFO. The formulation is typically at least about 5%, 7.5% or 10% nanoparticles comprising the active agent, and not more than about 25%, 15%, or 12.5% nanoparticles comprising the active agent, where the balance is a physiologically compatible carrier.

The formulations of the invention include both a nanoparticle composition, and a suspension thereof that provides a chelator suspension suitable for topical contact with internal organs, which organs may include lungs. The chelator formulation is a suspension of nanoparticles in a carrier that is biologically compatible, particularly compatible with tracheal tissue. Oil carriers of interest include medium chain trigyclerides, e.g. labrafac, while alternative carriers of interest include solutions of sorbitol, propylene glycol, glycerol, 1,3-butanediol, etc.

To generate the nanoparticles, the active agent, e.g. a pharmaceutical grade drug, is dissolved or suspended in a solvent appropriate for the drug, e.g. water, ethanol, methanol, acetone, etc. One of skill in the art can select a suitable solvent for the active agent of interest. The active agent can be admixed with a nanoparticle stabilizer, e.g. lecithin, albumin, and the like as described above in solution, or as a dry powder prior to combining with solvent. The combined active agent and stabilizer(s) form a nanoparticle suspension, which is precipitated, e.g. by lyophilization. The resulting nanoparticles, comprising drug and stabilizer, are collected. They are optionally dried. The nanoparticles are then mixed with a suitable carrier to provide for the formulation.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure. The effective amount of a therapeutic composition to be given to a particular patient will depend on a variety of factors, several of which will be different from patient to patient. Empirical methods may be used to determine the effective amount of therapeutic agent for treating a specific individual. The compositions can be administered to the subject in a series of more than one administration, or may be administered to the target tissue during periods of chronic graft rejection episodes.

Those of skill will readily appreciate that dose levels can vary as a function of the specific compound, the severity of the symptoms and the susceptibility of the subject to side effects. Some of the drugs are more potent than others. Preferred dosages for a given agent are readily determinable by those of skill in the art by a variety of means. A preferred means is to measure the physiological potency of a given compound.

Methods of Administration

Solid organ transplantation involves the removal of a diseased or otherwise dysfunctional organ from an individual, and replacing with a donor tissue. In the process of transplantation, particularly lung transplantation, it can be desirable to increase neovascularization at the site of anastomosis.

Of particular interest is the transplantation of a lung or lungs. In such procedures, a site, e.g. of anastomosis, including without limitation the trachea, is treated with an effective dose of a formulation of the present invention for the purpose of increasing neovascularization. During the surgical procedure, the formulation of the invention is topically applied to the surfaces of the target tissue, usually from about 0.1 to 50 ml. is used, and any convenient method of application, e.g. soaking, brush, spray, droplet, etc. In some embodiments the graft is briefly soaked or otherwise exposed to the formulation prior to implantation. Of particular interest is topical application of the chelator formulation to the region of tracheal anastomosis in lung transplantation, where the airways of both graft and recipient may be applied with the formulation. Following application of the chelator formulation, the surgical procedure is completed. The transient iron chelation improves the vascularization of the graft, providing for improved long-term graft function.

Frequently the lungs are obtained from a deceased donor although living donors are appropriate in some procedures, and the recipient and graft will be matched for HLA type as is conventional in the art. Typically the recipient will also be treated in accordance with conventional methods for immunosuppression, i.e. the treatment of a graft recipient with agents, primarily to diminish the immune responses of the host immune system against the graft. Immunosuppressive treatment of the transplantation patient begins with the induction phase, perioperatively and immediately after transplantation. Maintenance therapy then continues. Induction and maintenance strategies use different medicines at specific doses or at doses adjusted to achieve target therapeutic levels to give the transplantation patient the best hope for long-term graft survival.

Lung transplantation is appropriate in patients with irreversible, progressively disabling, end-stage pulmonary disease whose life expectancy is projected to be less than 12 to 18 months, despite the use of appropriate medical or alternative surgical therapies. A number of disease etiologies causing pulmonary failure treated with lung transplantation are known, e.g. cystic fibrosis, chronic obstructive pulmonary disease (COPD), primary pulmonary hypertension, etc. With some of these diseases, certain parameters have been used to predict survival without transplantation and such algorithms may be used in the selection of an individual for transplant, although clinical judgment often is necessary to determine when transplantation is appropriate. Consideration of transplantation should be undertaken in patients who are oxygen dependent and are demonstrating progressive deterioration in pulmonary function with increasing oxygen requirements or those who have had life-threatening events such as respiratory failure requiring mechanical ventilation, syncope, or massive hemoptysis.

A variety of oxygen-free radical scavengers, including deferoxamine, dimethyl thiourea, superoxide dismutase, and catalase, as well as modifications of the reperfusion environment using leukocyte depletion techniques or inhibitors of leukocyte binding and migration have been shown to improve lung graft function in a variety of experimental models during a period of cold ischemia following harvesting of the organ.

The surgical attachment of the graft is performed in accordance with conventional methods, for example the implantation of the donor lung may begin with the bronchial anastomosis. The donor bronchus is divided two rings proximal to the upper lobe orifice. The membranous bronchus is approximated using an absorbable, monofilament suture in a running fashion. The smaller cartilaginous bronchus is intussuscepted one or two rings into the larger bronchus using a modified horizontal mattress suture technique. The pulmonary arterial anastomosis is created using a running nonabsorbable monofilament suture. At this point, or immediately prior to creation of the anastomosis, the formulation may be applied, i.e. contacted directly with the involved tissues. After completion of the anastomoses and confirmation of hemostasis, the patient is weaned from CPB, if it had been required.

Fiber optic bronchoscopy may be performed to evaluate the anastomosis and to ensure patency of the airways and to monitor the graft over a period of time. As a follow up the patient is optionally evaluated for microvascular anastomosis formation and microvascular perfusion at the transplanted organ, for example in improving airway microvascular perfusion after a period of from about 3 to about 10 days, relative to a control transplant in the absence of treatment with the methods of the invention.

Kits and Packaging

In some embodiments, formulations are provided for use in the methods of the invention. Such formulations may comprise a stabilized nanoparticle of an iron chelating agent, including without limitation DFO, DFX, DFP, etc., which can be provided in a packaging suitable for clinical use, including packaging as a lyophilized, sterile powder; packaging of a stable suspension of active agent, for example nanoparticles, in carrier; separate packaging of nanoparticles and carrier suitable for mixing prior to use; and the like. The packaging may be a single unit dose, providing an effective dose of an iron chelator active agent in nanoparticle form in the manufacture of a medicament for improving the function of a solid organ transplant, wherein the medicament is topically applied to the surface of tissues at the site of anastomosis, usually immediately prior to, or at the time of transplantation surgery.

The pharmaceutical formulation of the invention may be packaged for use during surgery in a sterile unit dose, optionally with applicator, and may include labeling and/or instructions for use. Applicators may include a spray device, brush, dropper, etc. as known in the art.

EXPERIMENTAL

Microvascular Circulation and Lung Transplantation

Recent autopsy studies of lung transplants reveal a marked loss of microvasculature in the pre-obliterative bronchiolitis (pre-OB) foci of human lung transplants, which suggests that a loss of microcirculation and airway ischemia precede the onset of OB. Clinical studies from other solid organ transplants, such as liver and kidney, also demonstrate that chronic rejection develops after a loss of functional microvasculature. In a preclinical model of lung transplantation, it has been have shown that without immunosuppression, acute rejection eventually results in rejection of the donor microvasculature and a complete cessation of blood flow to the transplant. These clinical and preclinical findings cumulatively suggest that loss of the microvascular circulation may be a fundamental cause of loss of function.

Ischemia is the principal stimulus that induces neovascularization. Expression of virtually all proangiogenic growth factors is induced by hypoxia through the transcriptional activity of HIF-1. HIF-1 is a heterodimer composed of a constitutively expressed HIF-1β subunit and an oxygen-regulated HIF-1α subunit. AdCA5, an adenovirus vector encoding a constitutively active form of HIF-1α, has been demonstrated in several animal models to promote angiogenesis and accelerate recovery from tissue ischemia. HIF-1-mediated transcriptional responses orchestrate the expression of proangiogenic growth factors that facilitate angiogenesis by directly activating resident endothelial cells as well as recruiting circulating angiogenic cells.

OTTs undergoing acute rejection are relatively hypoxic compared with nonrejecting tracheal tissue, and undergo sequential damage characterized first by microvascular injury, followed by airway ischemia, and finally, reperfusion with active neovascularization. Recent clinical studies revealed that human lung transplant airways also are relatively hypoxic at baseline compared with both native (diseased) and control airways. During rejection increased hypoxia and ischemia may trigger an adaptive response to promote neovascularization of the allograft through activation of HIF-1α. HIF-1α consequently may be one of the central factors that help to maintain a functional microvasculature in transplanted organs.

Methods of preserving a functional microvasculature were studied, using efforts to delay donor loss of functional microvasculature by efforts to promote donor microvasculature integrity. Transient HIF-1α gene overexpression prolongs microvascular perfusion of airway allograft and alleviates tissue hypoxia. HIF-1α deficiency led to an accelerated loss of airway microvasculature. Therefore, application of a HIF-1 potentiating agent may be studied by chelator formulation delivery directly to the tissues at the time of transplantation.

Example 2

Prolonged Transplant Survival by HIF-α Stabilizing Iron Chelator Formulations

We have made nanoparticles dispersed in oil that is compatible with tracheal tissue. Nanoparticles were formed by the emulsion of drug in labrafac. The emulsion was stabilized by adding lecithin, chitosan, proalbumin, PVP and poloxamer. Stabilized solution was cryo-frozen and lyophilized to obtain the nanoparticles. The particles were suspended in labrafac lipophile to obtain the chelator formulation. Compositions and methods used in developing the chelator formulations are given below.

Example 3

Deferoxamine and Deferasirox Nanocapsule Formulations

| DFO 1: | | | | | |
|---|---|---|---|---|---|
| A DFO | B Lecithin | C Polaxamer-188 (0.5% Aq.) | D Chitosan-5K (0.5% Aq. | E Labrafac CC | F PVP-10K (40% Aq.) |
| %19.75 mg 200 | 19.75 200 | 19.75 200 (40 ml) | 1.23 12.5 (2.5 ml) | 29.63 300 | 9.88 100 (2.5 ml) |

DFO nanocapsules were prepared by a series mixing steps under stirring and bath sonication conditions followed by deep freezing and freeze drying. Briefly, 200 mg of DFO, 200 mg of lecithin and 300 mg of labrafac lipophile were mixed to form a first mixture; then 40 mL of 0.5% aqueous solution of Polaxamer-188 were added to form a first homogeneous liquid; 2.5 mL of 0.5% aqueous solution of chitosan-5K were added to form a second homogeneous liquid followed by adding 2.5 mL of 40% aqueous solution of PVP-10K to form a final homogeneous liquid. The final homogeneous liquid was freeze dried to obtain dry nanocapsules.

| BLA1: | | | | | |
|---|---|---|---|---|---|
| A DFO | B Lecithin | C Polaxamer-188 (0.5% Aq.) | D Chitosan-5K (0.5% Aq. | E Labrafac CC | F PVP-10K (40% Aq.) |
| %0 mg 0 | 24.62 200 | 24.62 200 (40 ml) | 1.54 12.5 (2.5 ml) | 36.92 300 | 12.31 100 (2.5 ml) |

The blank nanocapsules were prepared without DFO.

| DFX1 | | | | | |
|---|---|---|---|---|---|
| A DEF | B Lecithin | C Polaxamer-188 (0.5% Aq.) | D Chitosan-5K (0.5% Aq. | E Labrafac CC | F PVP-10K (40% Aq.) |
| %19.75 mg 200 | 19.75 200 | 19.75 200 (40 ml) | 1.23 12.5 (2.5 ml) | 29.63 300 | 9.88 100 (2.5 ml) |

DFX nanocapsules were prepared by a series mixing steps under stirring and bath sonication conditions followed by deep freezing and freeze drying. Briefly, a mixture of DFX and lecithin was obtained by dissolving 200 mg of DEX and 200 mg of lecithin in 10 mL of methanol/acetone (1:10) followed by removal of solvents in a rotary evaporator; then 40 mL of 0.5% aqueous solution of Polaxamer-188 and 300 mg of labrafac lipophile were added to form a first homogeneous liquid; 2.5 mL of 0.5% aqueous solution of chitosan-5K were added to form a second homogeneous liquid followed by adding 2.5 mL of 40% aqueous solution of PVP-10K to form a final homogeneous liquid. The final homogeneous liquid was freeze dried to obtain dry nanocapsules.

| DFO2: | | | | | |
|---|---|---|---|---|---|
| A<br>DFO | B<br>Lecithin | C<br>Polaxamer-188<br>(0.5% Aq.) | D<br>Probumin<br>(0.5% Aq.) | E<br>Labrafac<br>CC | F<br>PVP-10K<br>(40% Aq.) |
| %19.75<br>mg 200 | 19.75<br>200 | 19.75<br>200 (40 ml) | 1.23<br>12.5 (2.5 ml) | 29.63<br>300 | 9.88<br>100<br>(2.5 ml) |

DFO nanocapsules were prepared by a series mixing steps under stirring and bath sonication conditions followed by deep freezing and freeze drying. Briefly, 200 mg of DFO, 200 mg of lecithin, and 300 mg of labrafac lipophile were mixed to form a first mixture; then 40 mL of 0.5% aqueous solution of Polaxamer-188 were added to form a first homogeneous liquid; 2.5 mL of 0.5% aqueous solution of probumin were added to form a second homogeneous liquid followed by adding 2.5 mL of 40% aqueous solution of PVP-10K to form a final homogeneous liquid. The final homogeneous liquid was freeze dried to obtain dry nanocapsules.

| BLA2: | | | | | |
|---|---|---|---|---|---|
| A<br>DFO | B<br>Lecithin | C<br>Polaxamer-188<br>(0.5% Aq.) | D<br>Probumin<br>(0.5% Aq. | E<br>Labrafac<br>CC | F<br>PVP-10K<br>(40% Aq.) |
| %0<br>mg 0 | 24.62<br>200 | 24.62<br>200 (40 ml) | 1.54<br>12.5 (2.5 ml) | 36.92<br>300 | 12.31<br>100 (2.5 ml) |

The blank nanocapsules were prepared without DFO.

| 6.DFX2: | | | | | |
|---|---|---|---|---|---|
| A<br>DEF | B<br>Lecithin | C<br>Polaxamer-188<br>(0.5% Aq.) | D<br>Probumin<br>(0.5% Aq.) | E<br>Labrafac<br>CC | F<br>PVP-10K<br>(40% Aq.) |
| %19.75<br>mg 200 | 19.75<br>200 | 19.75<br>200 (40 ml) | 1.23<br>12.5 (2.5 ml) | 29.63<br>300 | 9.88<br>100<br>(2.5 ml) |

DFX nanocapsules were prepared by a series mixing steps under stirring and bath sonication conditions followed by deep freezing and freeze drying. Briefly, a mixture of DFX and lecithin was obtained by dissolving 200 mg of DFX and 200 mg of lethicin in 10 mL of methanol/acetone (1:10) followed by removal of solvents in a rotary evaporator; then 40 mL of 0.5% aqueous solution of Polaxamer-188 and 300 mg of labrafac lipophile were added to form a first homogeneous liquid; 2.5 mL of 0.5% aqueous solution of probumin were added to form a second homogeneous liquid followed by adding 2.5 mL of 40% aqueous solution of PVP-10K to form a final homogeneous liquid. The final homogeneous liquid was freeze dried to obtain dry nanocapsules.

| DFO3: | | | | |
|---|---|---|---|---|
| A<br>DFO | B<br>Lecithin | C<br>Polaxamer-188<br>(0.5% Aq.) | D<br>Probumin<br>(0.5% Aq. | E<br>Labrafac CC |
| %21.92<br>mg 200 | 21.92<br>200 | 21.92<br>200 (40 ml) | 1.37<br>12.5 (2.5 ml) | 32.88<br>300 |

DFO 3 nanocapsules were prepared by a series mixing steps under stirring and bath sonication conditions followed by deep freezing and freeze drying. Briefly, 200 mg of DFO, 200 mg of lecithin, and 300 mg of labrafac lipophile were mixed to form a first mixture; then 40 mL of 0.5% aqueous solution of Polaxamer-188 were added to form a first homogeneous liquid; 2.5 mL of 0.5% aqueous solution of probumin were added to form a second homogeneous liquid. The second homogeneous liquid was freeze dried to obtain dry nanocapsules.

| BLA3: | | | | |
|---|---|---|---|---|
| A<br>DFO | B<br>Lecithin | C<br>Polaxamer-188<br>(0.5% Aq.) | D<br>Probumin<br>(0.5% Aq.) | E<br>Labrafac<br>CC |
| %0<br>mg 0 | 28.01<br>200 | 28.01<br>200 (40 ml) | 1.75<br>12.5 (2.5 ml) | 42.1<br>300 |

The blank nanocapsules were prepared as same as DFO3 nanocapsules without DFO.

| DFX3: | | | | |
|---|---|---|---|---|
| A<br>DEX | B<br>Lecithin | C<br>Polaxamer-188<br>(0.5% Aq.) | D<br>Probumin<br>(0.5% Aq.) | E<br>Labrafac CC |
| %21.92<br>mg 200 | 21.92<br>200 | 21.92<br>200 (40 ml) | 1.37<br>12.5 (2.5 ml) | 32.88<br>300 |

DFX3 nanocapsules were prepared by a series mixing steps under stirring and bath sonication conditions followed by deep freezing and freeze drying. Briefly, a mixture of DFX and lecithin was obtained by dissolving 200 mg of DFX and 200 mg of lecithin in 10 mL of methanol/acetone (1:10) followed by removal of solvents in a rotary evaporator; then 40 mL of 0.5% aqueous solution of Polaxamer-188 and 300 mg of labrafac lipophile were added to form a first homogeneous liquid; 2.5 mL of 0.5% aqueous solution of probumin were added to form a second homogeneous solution. The final homogeneous solution was freeze dried to obtain dry nanocapsules.

Example 4

Chelator Formulations

To prepare DFO or DFX nanoparticle formulation, 1 g of DFO(X), BLA(X) and DFX (X) nanoparticles prepared as above were mixed well with 9 g of labrafac lipophile (Gattefosse SAS) with a stirring rod in a weighing boat and then the mixture was transferred into a 20 mL of plastic tube, followed by vortexing.

Administration of the formulation significantly increases airway microvascular perfusion during early times following transplantation. Since the vascular health is predictive for the health of the transplant, these data strongly suggest that this topical formulation is beneficial for the long term health of the transplant.

DFO formulation was administered around the donor trachea, the blood perfusion unit was measured 3 days following transplantation. Results are shown in FIG. 1.

Example 5

Deferoxamine (DFO) Nanoparticles Promote Airway Anastomotic Microvascular Regeneration and Alleviate Airway Ischemia Airway tissue ischemia and hypoxia in human lung transplantation is a consequence of the sacrifice of the bronchial circulation during the surgical procedure and is a major risk factor for the development of airway anastomotic complications. Augmented expression of HIF-1α promotes microvascular repair and alleviates allograft ischemia and hypoxia. DFO is an FDA-approved iron chelator which has been shown to upregulate cellular HIF-1α. Here, we developed a nanoparticle formulation of DFO that can be topically applied to airway transplants at the time of surgery. In a mouse OTT model, the DFO nanoparticle was highly effective in enhancing airway microvascular perfusion following transplantation through the production of the angiogenic factors, placental growth factor (PLGF) and stromal cell-derived factor (SDF)-1. The endothelial cells in DFO treated airways displayed higher levels of p-eNOS and Ki67, less apoptosis, and decreased production of perivascular reactive oxygen species (ROS) compared to vehicle-treated airways. In summary, a novel DFO formulation topically-applied at the time of surgery successfully augmented airway anastomotic microvascular regeneration and the repair of alloimmune-injured microvasculature. This approach may be an effective topical transplant-conditioning therapy for preventing airway complications following clinical lung transplantation.

We hypothesized that enhancing HIF-1α expression through local administration of DFO would accelerate anastomotic microvascular regeneration, alleviating tissue ischemia and hypoxia with the potential to promote the health of the anastomosis and to limit post-transplant airway complications. To test this, we created a lipid nanoparticle formulation of DFO that may be applied topically to airway anastomoses and studied its effect in the mouse OTT model.

Drug-loaded nanoparticles have emerged as a promising strategy for efficient drug delivery for the treatment of a variety of diseases. Drugs encapsulated in nanoparticles may have increased bioavailability due to higher specific surface area and biocompatibility of the formulated particles with the tissue. Specifically, lipid nanoparticles are becoming an important formulation strategy because of their small size, biodegradable nature, and high versatility. One commonly used compound for the formulation of lipid nanoparticles is lecithin, which is a natural lipid mixture of phospholipids and biocompatible excipients. Propylene glycol is a small molecule metabolized in the liver and is commonly used in food production. It is "generally recognized as safe" (GRAS) by the FDA. An extensive body of published literature has also addressed the safety issues regarding the systemic exposure to propylene glycol.

To improve the bioavailability of these drugs to the donor trachea and the anastomotic ends of the recipient trachea, we formulated these two compounds in lecithin nanoparticles with propylene glycol as the carrier. We then characterized those formulations with atomic force microscopy (AFM) and scanning electron microscopy (SEM), aided by Raman spectroscopy. Nanoparticle penetration into the trachea tissue was assessed by fluorescent confocal microscopy and mass spectroscopy of tissue sections. We lastly examined the in vivo effect of nanoparticles on anastomotic airway microvascular regeneration and promotion of airway blood flow. This study demonstrated that tissue ischemia can be limited by local administration of nanoparticles designed to enhance HIF-1α expression.

Material and Methods

Preparation of Nanoparticle Formulations.

Analytical grade DFO was purchased from Sigma (St. Louis, Mo.). Lecithin was obtained from the soft-gels nutritional supplement made by Finest Natural and distributed by Walgreens. Diagnostic grade probumin was purchased from Millipore (Billerica, Mass.). All solvents used were reaction grade. To prepare the DFO dry powder, equal amounts of DFO and lecithin (48.49% each, by weight) were mixed with a 0.5% aqueous solution of probumin (3.02% by weight). The solution was stirred vigorously until a fine suspension was achieved; this suspension was then lyophilized. A control formulation containing only the vehicle was prepared by making a fine suspension of lecithin (94.14% by weight) in a 0.5% aqueous solution of probumin (5.86% by weight). The liquid suspension was then lyophilized. The final nanoparticle solution was prepared by mixing the dry powders with a 1:9 (w/v) ratio of 40% propylene glycol in deionized water.

Mice.

All animal procedures were approved by Stanford's Administrative Panel on Laboratory Animal Care (APLAC) and/or the VA Palo Alto Institutional Animal Care and Utilization Committee (IACUC). All mice including C57BL/6J (B6; H-2b), Balb/C (H-2d) were purchased from Jackson Laboratory.

Scanning Electron Microscopy (SEM).

Characterization of dry powders. All fixatives used in the preparation of samples for scanning electron microscopy were obtained from Electron Microscopy Sciences (Hatfield, Pa.). Nanoparticle formulations in propylene glycol solution were drop-casted onto an SEM sample stub with a double-sided carbon tab and then air dried at room temperature. The deposited powder was then sputter-coated with an Au—Pd film (7 nm in thickness) in a Denton Desk II machine (Denton Vacuum, NJ), and imaged with a Hitachi S-3400N VP-SEM (Hitachi High Technologies, TX), using secondary electron (SE) detection, operated at 10-15 kV.

Assessment of the tracheal microstructure following incubation in nanoparticle formulations. Whole tracheas were harvested from BALB/c mice and transferred to 1×PBS on ice. The tracheas were incubated in nanoparticle solutions at 37° C. for 10 minutes in a humidified chamber. The tubular tracheal sections were rinsed in 1×PBS twice, blot dried and fixed overnight in 4% paraformaldehyde with 2% glutaraldehyde in 0.1 M sodium cacodylate buffer (pH7.4). Tissues were gently washed twice with the same buffer, and then post-fixed in 1% aqueous osmium tetroxide ($OsO_4$) for one hour. Samples were then washed twice in purified water, and dehydrated in a series of increasingly concentrated ethanol rinses (50%, 70%, 90%, 100%, each rinse twice and 15 min per rinse). The specimens were finally critical-point dried (CPD) in liquid $CO_2$, in a Tousimis 815B critical point dryer (Tousimis Rockville Md.). CPD-dried samples were mounted on 45° angled SEM stubs with adhesive copper tape and sputter-coated with 4 nm of Au—Pd, as described above. Minimal contact with the tissues was ensured to avoid the destruction of the fine structures. The adventitial and mucosal layers of the sections were examined with a Zeiss Sigma field emission SEM (FESEM) (Carl Zeiss, Inc., Thornwood, N.Y.) operated at 2-3 kV, using InLens SE detection.

HPLC-MS Analysis for Drug Penetration into Tracheas.

Sample preparation. Determination of the kinetics of the chelator suspension absorption into tracheal tissue. Whole tracheas were harvested from BALB/c mice and transferred to 1×PBS on ice. Each trachea (3~4 mg dry weight) was cut evenly into 3 or 4 cross-sectional segments. Tracheal segments were then dipped in DFO formulation for 3 seconds, blot dried to remove excessive solution and incubated in a humidified chamber at 37° C. for 0, 10, 30 and 60 minutes. After incubation, the segments were rinsed in 1×PBS twice and digested in 50 it of 0.75 mg/ml Liberase TL (Roche Applied Science, IN) in $H_2O$ at 37° C. overnight. Digested tissues were further homogenized by sonication.

Preparation of pig and human trachea for chelator formulation penetration analysis. After 4 hours incubation in DFO or DFX nanoparticle solution, pig and human trachea sections were prepared by lateral sectioning. Sections (0.5 mm each) were collected and digested with 3 volumes (v/w) of Liberase TL (0.75 mg/ml in $H_2O$) overnight at 37° C. Samples of trachea lysate were vortexed and homogenized with a probe sonicator.

For all types of tracheal tissues, 50 μl of acetonitrile (100 μl) was added to the tissue homogenate to extract DFO. The samples were then centrifuged and the supernatant was diluted (1:20 to 1:100) in 50% acetonitrile and transferred to HPLC vials.

HPLC-MS/MS analysis. Preparation of HPLC-MS/MS standards. All chemicals and solvents for HPLC-MS/MS were purchased from Sigma (St. Louis, Mo.) or Fisher Scientific (Hampton, N.H.). Stock standard solutions of DFO were prepared by dilution of accurately weighed powders in DMSO. Calibration spiking solutions were prepared by diluting the stock solution with methanol: water (1:1, v/v) to final concentrations of 50, 20, 10, 5, 2, 1, 0.500, 0.200, and 0.100 μg/mL of DFO. Standard spiking solutions (30 μl) were added into vehicle treated tracheal section homogenates and processed with each batch of unknown samples. Chromatograms for standards were used to establish characteristic retention times (RTs) of DFO, and verified that the MS signal was linear over the range of 0.1-50 μg/ml in tracheal section homogenates. The peak areas of DFO were calculated and plotted against the concentration of the calibration standards. Calibration curves were generated using the least squares linear regression method with Analyst® 1.5.1 software.

HPLC-MS/MS data acquisition. For DFO separation and detection, the flow rate was set at 300 μl/min. Chromatographic separation was performed on an Ascentics ES Cyno column (Sigma, St. Louis, Mo.). A 2.5-minute elution was performed with a 20-90% gradient of 0.1% formic acid in acetonitrile as mobile phase B; mobile phase A was 5 mM ammonium acetate/0.1% formic acid in water. After 3 minutes, % B was changed to 20% and kept for 1 minute. The HPLC was directly coupled to an AB SCIEX 4000 QTRAP triple quadrupole mass spectrometer with electrospray ionization. To monitor DFO, the mass spectrometer was operated in the positive multiple reactions monitoring mode, with transitions of 561.17/102.30 and 560.79/201.00 Da. The switching valve diverted HPLC flow to the mass spectrometer at 0.4-3 minutes. The elution time for DFO was 0.7 minutes.

HPLC-MS/MS data analysis. Peak detection, integration and data processing were performed with the AB SCIEX Analyst 1.5.1 software package. Concentrations of DFO were calculated by plotting the peak area of unknown samples against the calibration curve prepared in the corresponding matrix. A 1/x weighted linear regression was used to calculate the unknown DFO concentrations.

Raman Spectroscopy and Atomic Force Microscopy (AFM) Imaging.

Both Raman and AFM were performed using NTEGRA Spectra combined AFM-Raman system (NT-MDT). For individual particle Raman scanning, dry lyophilized propylene glycol particle cluster was gently tapped against the surface of pre-cleaned Si wafers. Tissue samples for Raman scanning were made by spreading the nanoparticle solution on tissue patches (about 7×7 mm), which were fixed to the surface of glass slides and allowed to dry. Raman measurements and confocal scanning of the nanoparticles applied to either Si wafers or tracheal tissues were performed in backscattering geometry with a long-working Mitutoyo objective (100×, 0.7 NA). The illumination light was 473 nm, and the power was kept at ~0.8 mW to minimize sample damage. Raman maps were produced with a step size of 0.5 μm and 1 s exposure. 600 gr/mm gratings were used for optimal signal and spectral resolution.

AFM imaging was performed in tapping mode with commercial cantilevers (k=5.4 N/m, R<10 nm) at 0.7 Hz. This provided surface topography and phase contrast images to discern stiffness of different areas within the islands. The locally equalized topography image was also obtained from the initial topography image by the AFM image analysis software, supplied with the instrument, to allow taller structures to be seen.

Analysis of Nanoparticle Cellular Localization.

Rhodamine B isothiocyanate (RBITC) was purchased from Sigma; 1,2-distearoyl-sn-glycero-3-phosphoethanolamine-poly(ethylene glycol)-amine (DSPE-PEG-NH2, Mw=3400) was purchased from Laysan Bio (Arab, Ala.) and the PD-10 desalting column was purchased from GE Healthcare. Rhodamine, a fluorescent marker, was linked to an inert lipid (DSPE) in the nanoparticle formulation. The linking reaction was performed by dissolving 34 mg (10 μM) of DSPE-PEG-NH2 and 15.6 mg (29.1 μM) of RBITC in a 1 ml solution of methanol:water (1:9, v/v). The reaction mixture was stirred overnight in a dark room at 4° C. The solution was then run through a PD-10 desalting column with MilliQ water to remove the unreacted RBITC. The labeled fractions were collected and lyophilized to obtain rhodamine-labeled DSPE. To prepare the fluorescent labeled nanoparticles, DSPE was mixed with 1% lecithin by weight. The labeled nanoparticles were administered on the inside and outside of the walls of tracheal samples, and then incubated at 37° C. for 4 hours. After incubation, they were washed 3 times with PBS, then embedded in OCT (Sakura Finetek) to make frozen sections. The tissue blocks were cut to 20 μm sections. Samples were stained with mounting media containing DAPI fluorescent dye and imaged with a Leica SP2 confocal fluorescence microscope.

Tracheal Transplantation.

Four to six week old BALB/c mice were used as donors and age and sex matched B6 mice were used as recipients. The surgical procedure of orthotopic tracheal transplantation was performed as previously described (see Jiang et al. (2011) J Clin Invest 121:2336-2349). Briefly, both donor and recipient mice were anesthetized with 50 mg/kg of ketamine and 10 mg/kg of xylazine. 5- to 7-ring tracheal segments were removed from donor mice. The donor tracheas were stored in PBS on ice prior to transplantation. A ~2-3 cm incision was made in the midline of the recipient's neck. The strap muscles were then bluntly dissected and retracted with 3-0 suture to allow clear exposure of the laryngotracheal complex. After the recipient trachea was transected, the donor graft was removed from the PBS, blot dried and then soaked in the chelator suspension for approximately 5 seconds. The trachea was removed of the solution and blot dried again to remove excess chelator suspension. The trachea was then sewn in with 10-0 nylon suture as previously described. Then, ~100 μl of chelator suspension was applied to the outer wall of the donor trachea and anastomoses. The skin was closed with 5-0 silk sutures.

Blood Perfusion Monitoring by Laser Doppler Flowmetry.

The procedure has been described in detail in Khan et al. (2012) *Am J Physiol Lung Cell Mol Physiol* 303:L861-869. In short, the transplanted mice were placed under general anesthesia and the tracheal grafts were carefully exposed using stay sutures to gently retract the strap muscles, revealing the anterior wall of the trachea. Perfusion monitoring was performed with a fiberoptic LDF probe connected to the OxyLab laser Doppler flowmetry (LDF) monitor (Oxford Optronix). This provides a continuous digital readout of blood perfusion units (BPUs) by real-time measurements of red blood cells in flux that is proportional to the red blood cell perfusion. The probe is connected to a micromanipulator and is gently lowered onto the outer surface of tracheal grafts and BPU measurements were recorded.

Tissue Preparation for Perfusion Studies and Immunohistochemistry.

For whole-mount tracheal microvascular analysis, mice were injected with 100 μl of FITC-conjugated tomato lectin (Vector Laboratories) at a concentration of 1 mg/ml. After 5 minutes of circulation, the mice were perfused with 1% PFA diluted in PBS for about 2 minutes until the outflow of the solution turned clear. The tracheas were then harvested, fixed in 1% PFA for 1 hour at 4° C., and then washed 3 times with PBS. Whole tracheas were mounted on glass slides in Vectashield H-1200 mounting medium (Vector Laboratories). Assessment of the percentage of the perfused area was carried out as previously described. Briefly, the whole tracheal allograft (every cartilaginous and inter-cartilaginous region) was examined and each area was scored either a 1 if it was perfused or 0 if it was not perfused. The percent perfusion was then calculated as follows: total score/total regions examined. Frozen sections were used for other immunohistochemistry analysis. Tracheal samples were snap-frozen in OCT solution (Sakura Finetek) and the samples were stored at −80° C. 8-μm sections were used for immunofluorescence staining. Anti-CD31 antibody (1:200; BD Pharmingen) was used to stain endothelial cells; anti-Ki67 antibody (1:100; BD Pharmingen) was used to stain proliferating cells; anti-p-eNOS antibody (1:100; Cell Signaling) was used to stain phosphorylated form of eNOS in endothelial cells. Dihydroethidium (DHE) (20 μM, Invitrogen) was used to detect reactive oxygen species (ROS). The TUNEL assay (Invitrogen, C10245) was carried out according to the manufacturer's protocol. Photomicrographs were taken with a Zeiss LSM 510 laser scanning confocal microscope with a Zeiss LSM Image Browser software. Quantification of the staining of Ki67, p-eNOS, dihydroethidium and TUNEL were performed with ImageJ software.

Quantitative Real Time RT-PCR.

Tracheal samples were incubated in RNAlater solution (Invitrogen) overnight at 4° C. Total RNA was then isolated using the QIAGEN Shredder and RNeasy Mini Kit (QIAGEN) as per the manufacturer's protocol. Total RNA (1 μg) was reverse transcribed with Moloney murine leukemia virus reverse transcriptase (Invitrogen) and 5 μM random hexamer primers according to the manufacturer's protocol. 2 μl of 1:10 diluted reverse transcription reactions were added to quantitative real time-PCR (qRT-PCR) reactions with 5 μl of 2×SYBR Green Master Mix (Applied Biosystems) and 100 nM of forward and reverse primers specific for the genes of interest in a total volume of 10 μl. Detection was carried out with the ABI Prism 7700 sequence detector (Applied Biosystems). SDS analysis software (Applied Biosystems) was used to analyze the data. Cyclophilin mRNA expression was used to normalize gene expression to account for sample-to-sample variation in input and reverse transcription efficiency. The $2^{-\Delta\Delta C_t}$ method was used to calculate fold changes. The primers used are listed in Table 1.

TABLE 1

| Gene | Forward Primer | Reverse Primer |
| --- | --- | --- |
| Tie2 | GTGTAGTGGACCAGAAGG | CTTGAGAGCAGAGGCATC |
| SDF-1 | GAGAGCCACATCGCCAGAG | TTTCGGGTCAATGCACACTTG |
| ANGPT1 | CTACCAACAACAACAGCATCC | CTCCCTTTAGCAAAACACCTTC |
| ANGPT2 | CTGTGCGGAAATCTTCAAGTC | TGCCATCTTCTCGGTGTT |
| VEGF | GGCTGCTGTAACGATGAAG | CTCTCTATGTGCTGGCTTTG |
| PLGF | GGATGTGCTCTGTGAATGC | CCTCTGAGTGGCTGGTTAC |
| 18S | GAATCGAACCCTGATTCCCCGTC | CGGCGACGACCCATTCGAAC |

Statistics.

Statistical analysis was performed using 2-tailed Student's t test, with a significance level of $p<0.05$.

Results

Structure and Morphology Analysis of Drug Nanoparticles.

DFO was formulated into encapsulated drug nanoparticles, drug powders and final topical solutions as shown in FIG. 1A. We chose the tracheal membrane-compatible lecithin to encapsulate the drugs to ensure their efficient delivery to the tissue. To assess the encapsulation efficiency, structural analysis of DFO before and after encapsulation was performed using Raman spectroscopy. A Raman spectrum of pure DFO was first examined (FIG. 1B). DFO molecules in the nanoparticle exhibited a spectrum different from that of pure DFO, with many bands merging together and becoming broader, which was likely due to strong hydrodynamic screening of DFO molecules and the disruption of its crystalline structure (FIG. 1C).

Next, SEM was used to study the morphology of the nanoparticles. To acquire SEM images of dry nanoparticle powder, 40% propylene glycol was first used to make the nanoparticle solution which was then deposited onto generic aluminum SEM sample stubs and air-dried in situ. The blank vehicle showed a generally homogeneous lecithin structure (FIG. 1D), and DFO nanoparticles also showed homogeneous semi-porous networks (FIG. 1E).

Chelator Nanoparticle Homogeneity.

Figure 2:
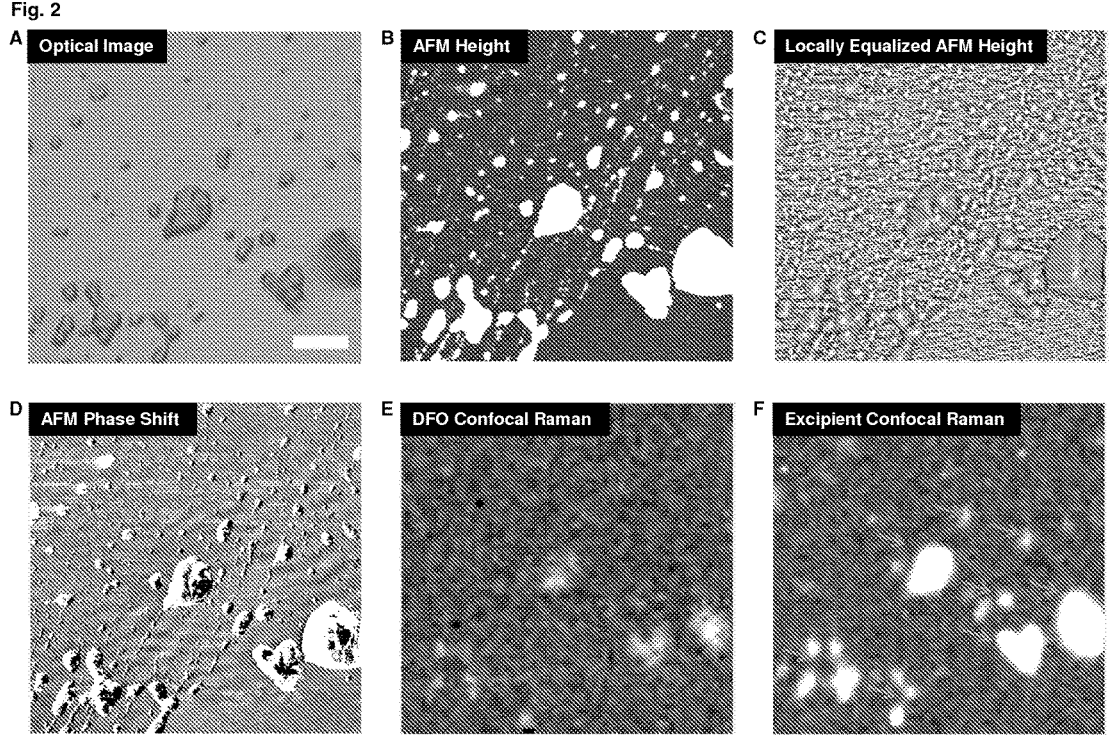
FIG. 2. Sample homogeneity analysis of DFO in nanoparticle islands on a Si wafer. A-F. DFO sample homogeneity was assessed by optical image (A), AFM height (B), locally equalized AFM height (C), AFM phase shift (D), confocal Raman maps of DFO (red arrows) (E) and the excipient (green arrows) (F). The Raman confocal maps were acquired by integrating the intensities of the following peaks: DFO peak centered at 1620 cm$^{-1}$ (1600-1640 cm$^{-1}$) (E) and excipient peak at 1655-1695 cm$^{-1}$ (F). Scale bar: 5 µm.

To determine the degree of homogeneity in the distribution of DFO within the nanoparticle, confocal Raman scanning and AFM imaging of small nanoparticle islands on the surface of Si wafers was performed. Sample material was loaded onto the surface of Si wafer to ensure the acquisition of high quality images, and imaging was performed under low power (<1 mW) to avoid sample damage. The optical image of DFO showed that the surface was covered by separate islands (FIG. 2A). The inner structure of the islands was probed by AFM scanning in tapping mode. AFM images showed the morphology and size of smallest nanoparticles, as well as larger nanoparticle aggregates (FIG. 2B-D). Confocal Raman images showed uniform distribution of the excipient and the DFO nanoparticle formulation as well as very good correlation between the distribution of DFO and excipient (FIG. 2E, F). These data together demonstrate that DFO was efficiently encapsulated in the excipient lecithin.

Microstructure Analysis of Chelator Treated Trachea.

Figure 9:
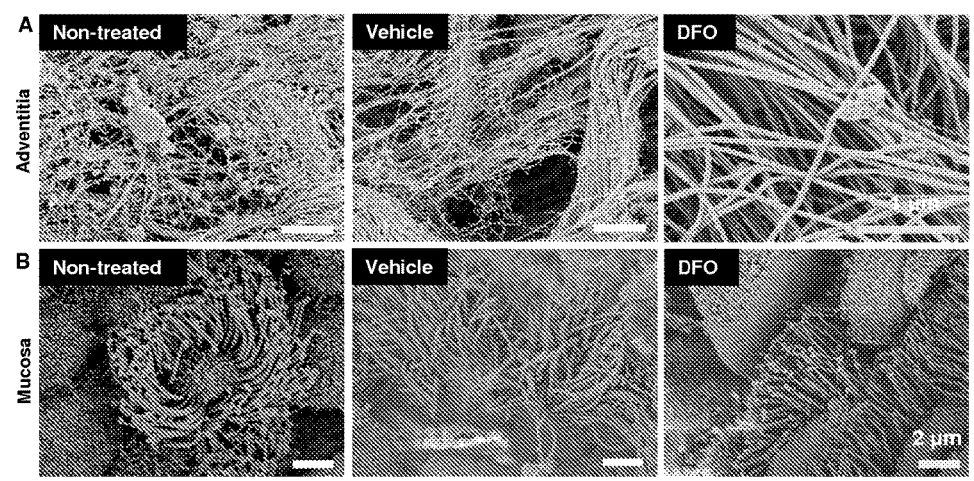
FIG. 9. SEM images of mouse tracheas following incubation in vehicle or nanoparticle solution. Tracheas were examined by SEM following a 10 min incubation in the nanoparticle solution. A, B. Adventitial layer (A) and mucosal layer (B) of non-, vehicle-, and nanoparticle-treated tracheas.

Although the main ingredients used in the nanoparticle formulation are considered safe, we wanted to confirm that the administration of the nanoparticles on the tracheal surface would not adversely affect tracheal microstructures. SEM was used to examine the morphology of the nanoparticle-treated tracheas. The images showed that the adventitial layer of the tracheas treated with vehicle or DFO solution were not significantly different from that of the untreated samples. Similar to the untreated tracheal samples, individual collagen fibrils displayed fine structures with lateral rings clearly visible (FIG. 9A). Also, the mucosal layer of the tracheas treated with vehicle or nanoparticles did not show any visible signs of damage (FIG. 9B). Only a few brushes were observed to be missing from the tops of some cilia bundles in treated samples; a finding likely caused by the capillary forces exerted by water during the nanoparticle solution washing process. Altogether, our data suggest that a 10 min incubation of tracheas in the nanoparticle formulation did not significantly affect the microstructure of the airway.

Drug Penetration into the Tracheal Tissue.

Figure 3:
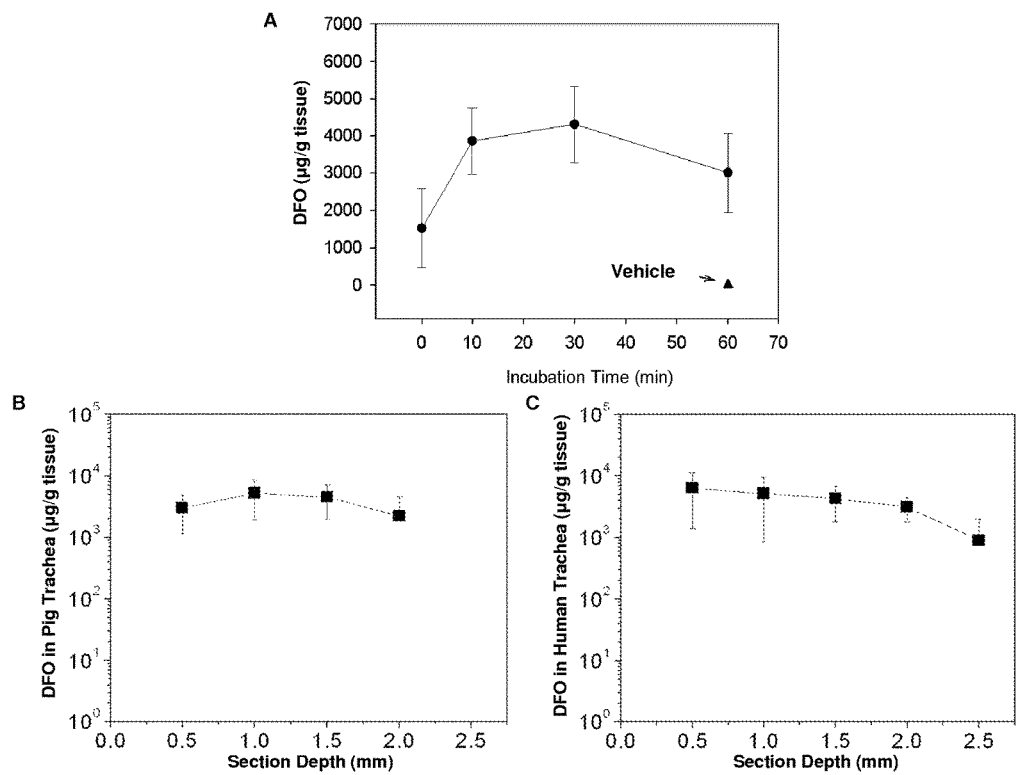
FIG. 3. Assessment of the nanoparticle penetration into tracheas. A. Kinetics of DFO nanoparticle penetration into mouse tracheas. B and C. Analysis of the depth of the nanoparticle penetration into pig (C) and human tracheas. The DFO concentrations were measured by HPLC (A to C). Data are shown as means±SEM.

We next assessed the drug nanoparticle penetration into the tracheal tissue. Examination of the penetration kinetics showed that the DFO nanoparticle achieved near-maximum penetration at 10 min of incubation, and reached a plateau when approaching 60 min (FIG. 3A). We then determined the depth of drug penetration and absorption by HPLC-MS/MS. Because mouse tracheas are relatively thin, we chose to use pig and human tracheas for these studies. Although the efficiency of penetration was variable, DFO nanoparticles were able to penetrate the pig and human tracheas (FIG. 3B, C). In the pig trachea, DFO penetrated to and was absorbed to a depth of 2 mm (FIG. 3B). A similar trend was also observed in the human trachea penetration depth analysis (FIG. 3C). These data suggest that the penetration of DFO is efficient in both species of mammalian tracheas examined.

Drug Penetration into Cytoplasm of the Tracheal Cells.

Figure 4:
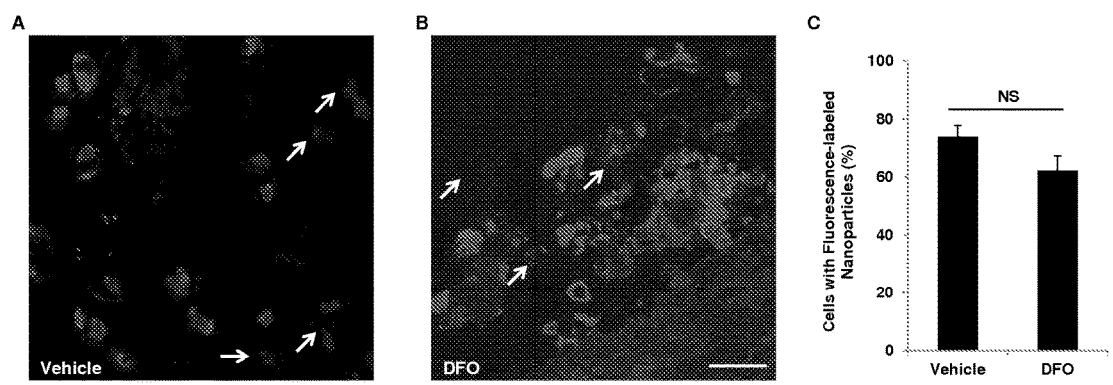
FIG. 4. Subepithelial cellular localization of nanoparticle formulations. A and B. Confocal microscopy images showing the subepithelial cellular distribution of vehicle alone nanoparticles (A) and DFO nanoparticles (B). C. Quantification of cellular nanoparticle localization by percentage of cells with cytoplasmic fluorescence. Red: Rhodamine-labeled DSPE-PEG identifies the lipid vehicles of the nanoparticles; Blue: Nuclear staining by DAPI. White arrows: cells with no cytoplasmic fluorescent signal. Data are shown as means±SEM. NS, not significant, Student's t test (C). Scale Bar: 20 µm (A, B).

To test the efficacy of drug absorption, we used confocal microscopy to determine the cellular localization of the drug nanoparticles. Because cells of the subepithelial layer play a more important role in angiogenesis, we examined the penetration of drug into these cells. Fluorescence-tagged vehicle was found to be localized in the cytoplasm of cells in tracheas treated with vehicle or DFO nanoparticles (FIG. 4A, B). Quantification showed that the percentages of fluorescence-positive cells were about 70% and 60% for the vehicle and DFO formulation respectively (FIG. 4C). Because the drugs were previously shown to be well-encapsulated by the vehicle (FIG. 1E), the fluorescence signal can be used to estimate the cellular localization of the drug molecules. These images confirmed that the DFO nanoparticle formulation efficiently penetrated the tissue and reached the cells in the subepithelial layer of the trachea.

Effects of DFO Chelator on Microvascular Anastomosis Formation and Airway Microvascular Perfusion.

Figure 5:
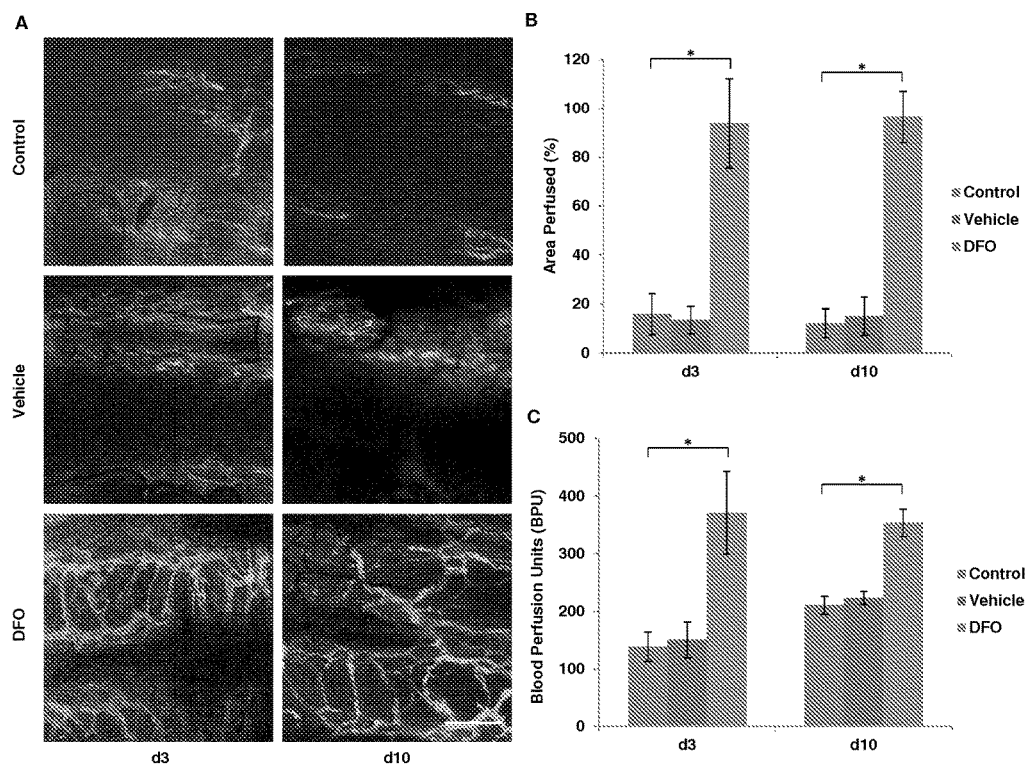
FIG. 5. Effects of DFO nanoparticle formulation on airway microvascular perfusion. A. Confocal microscopic imaging showing microvascular perfusion of non-, vehicle- and DFO nanoparticle-treated airway allografts at d3 and d10 following transplantation. B. Quantification of perfused airway microvasculature following transplantation. C. Airway blood perfusion measured by laser Doppler flowmetry at d3 and d10 following transplantation. Scale bar: 100 µm (A). Data are shown as means±SEM. *P<0.05, Student's t test (B, C).

The mouse OTT model has been shown to faithfully replicate lymphocytic bronchitis observed in lung transplant recipients, and is useful for studying phenomena associated with clinical airway complications. We have previously shown that the airway microvascular circulation can be easily studied in this model and that the perfusion of the airway allograft can be used to assess the regeneration of the injured airway microvasculature, particularly at the anastomosis. The airway allograft is transplanted en bloc, and there is no vascular perfusion prior to the formation of the microvascular anastomosis between the graft donor and the recipient. Therefore, earlier (i.e. day (d) 3 following transplantation) appearance of graft perfusion indicates an accelerated vascular anastomosis formation. In this model, airway perfusion loss around d10 is consistently observed and is primarily caused by alloimmune-mediated endothelial cells injury as previously described by Babu et al. (2007) *J Clin Invest* 117:3774-3785. Thus, persistent airway microvascular perfusion at d10 indicates more efficient repair of damaged vessels. FITC-lectin microvascular perfusion images showed that DFO treatment significantly increased airway perfusion at both d3 and d10 following transplantation (FIG. 5A), and the microvascular perfusion of vehicle treated allografts was not significantly differently from non-treated control transplants (FIG. 5A). Percentages of perfused areas of trachea allografts treated with DFO were >90% in contrast to <20% in control and vehicle treated airways at both d3 and d10 (FIG. 5B). The use of LDF for transplanted tracheal tissue blood perfusion was recently developed by our laboratory and has been previously used to assess airway perfusion. LDF showed that perfusion of the allograft treated with DFO was significantly higher at both d3 and d10 compared to control and vehicle treated grafts (FIG. 5C). These studies suggest that DFO nanoparticles accelerated airway microvascular anastomosis formation and promoted the repair of damaged vasculature.

Effects of DFO Nanoparticle on Angiogenic Factor Expression in Ischemic Airways.

Figure 6:
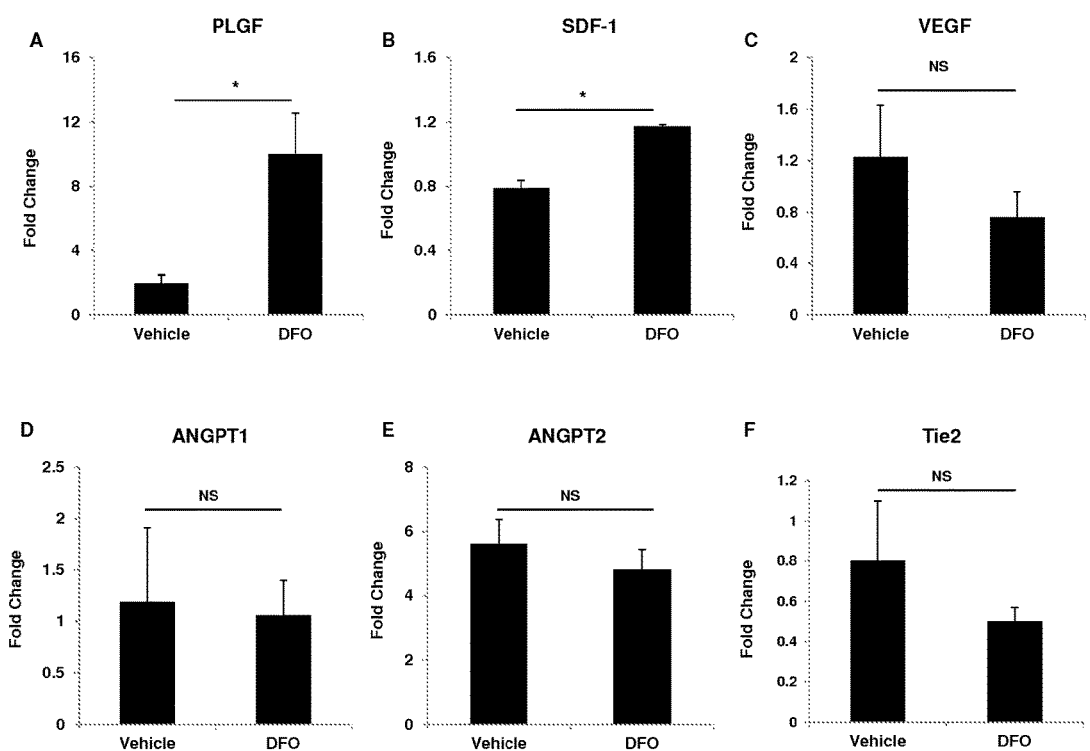
FIG. 6. Analysis of angiogenic growth factors and associated angiogenic cytokines. A-E. Real time RT-PCR analysis of mRNA expression of angiogenic growth factors in d3 airway allografts treated with vehicle or DFO nanoparticles (n=3-5). F. Real time RT-PCR analysis of Tie2 mRNA expression in d3 allografts treated with vehicle or DFO nanoparticles (n=3-5). Data are shown as means±SEM. NS, not significant; *P<0.05, Student's t test.
Figure 10:
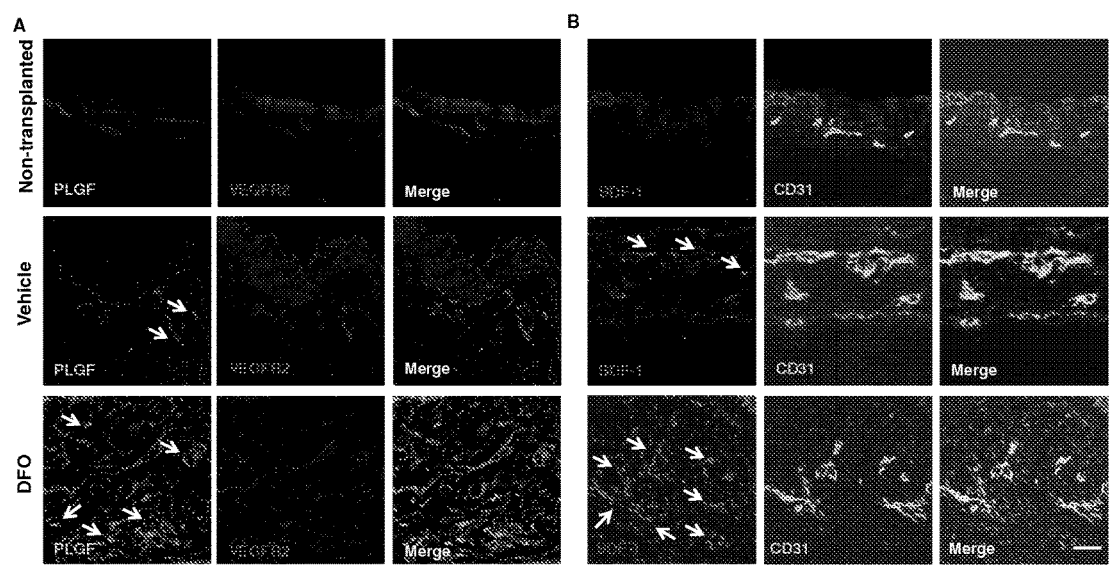
FIG. 10. Immunofluorescent staining of PLGF and SDF-1 in vehicle- or DFO-treated d3 airway allografts. A, B. Augmented PLGF staining (green, white arrows) (A) and SDF-1 staining (red, white arrows) (B) were observed in DFO-treated d3 allografts. VEGFR2 (A) and CD31 (B) were used to as endothelial cell markers. Scale bar: 20 µm.

We next asked how DFO promotes airway microvascular perfusion. Expression of angiogenic factors and cytokines are closely associated with neovascularization. Based on the observation that the promotion of vascular perfusion by DFO was most significant at d3 following transplantation, we isolated mRNA from d3 allografts and analyzed the expression of angiogenic factors and cytokines (PLGF, SDF-1, VEGF, ANGPT1 and ANGPT2) and the angiogenic receptor, Tie2 by quantitative real time RT-PCR. Expression of PLGF and SDF-1 was significantly increased (FIG. 6A, B), but there was no significant difference observed in the expression of angiogenic factors, VEGF, ANGPT1 and ANGPT2 or the Tie2 receptor (FIG. 6 C-F). Consistent with the results of the mRNA study, immunofluorescent staining showed that the levels of PLGF and SDF proteins were also increased (FIGS. 10 A and B). These data suggest that DFO likely promotes early microvascular anastomosis formation through the upregulation of angiogenic growth factors.

Effects of DFO Nanoparticles on Tracheal Endothelial Cells.

Figure 7:
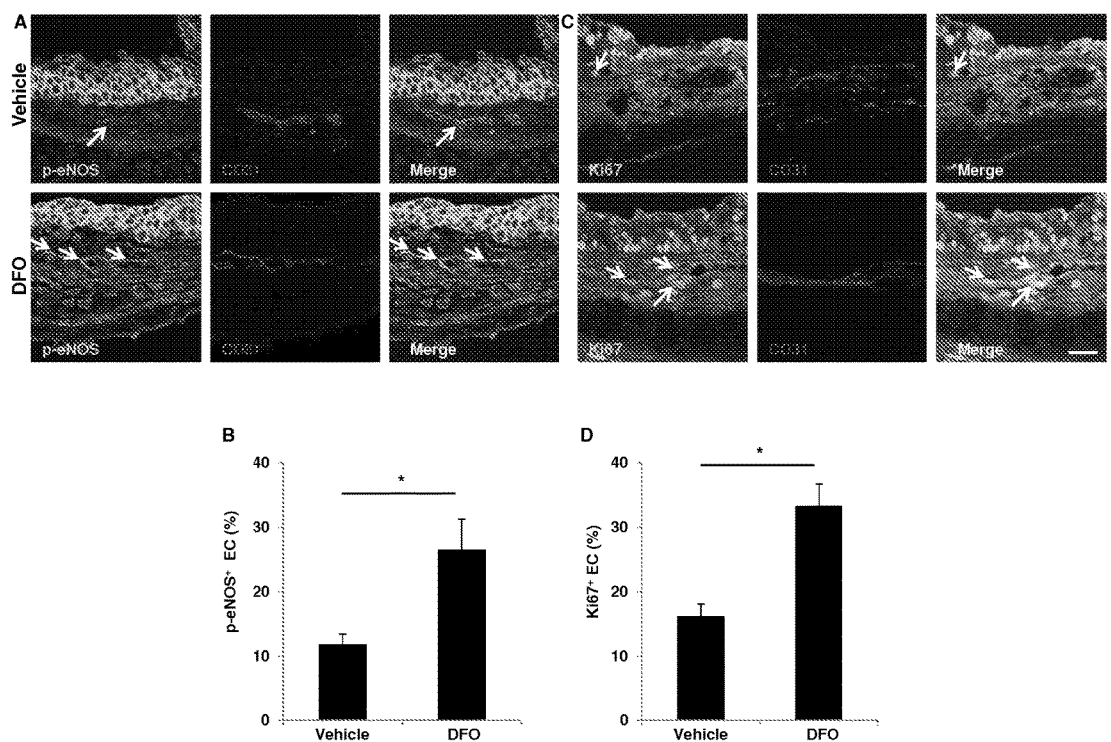
FIG. 7. Increased levels of p-eNOS and Ki67 in the endothelial cells of tracheas treated with DFO nanoparticles. A, C. Confocal microscopic images showing increased p-eNOS (green, white arrows) and Ki67 (green, white arrows) in ECs of DFO treated airways. B, D. Quantification of p-eNOS$^+$ cells and Ki67$^+$ cells (n=3-5). Scale bars: 20 µm (A, C). Data are shown as means±SEM. *P<0.05, Student's t test (B, D).
Figure 8:
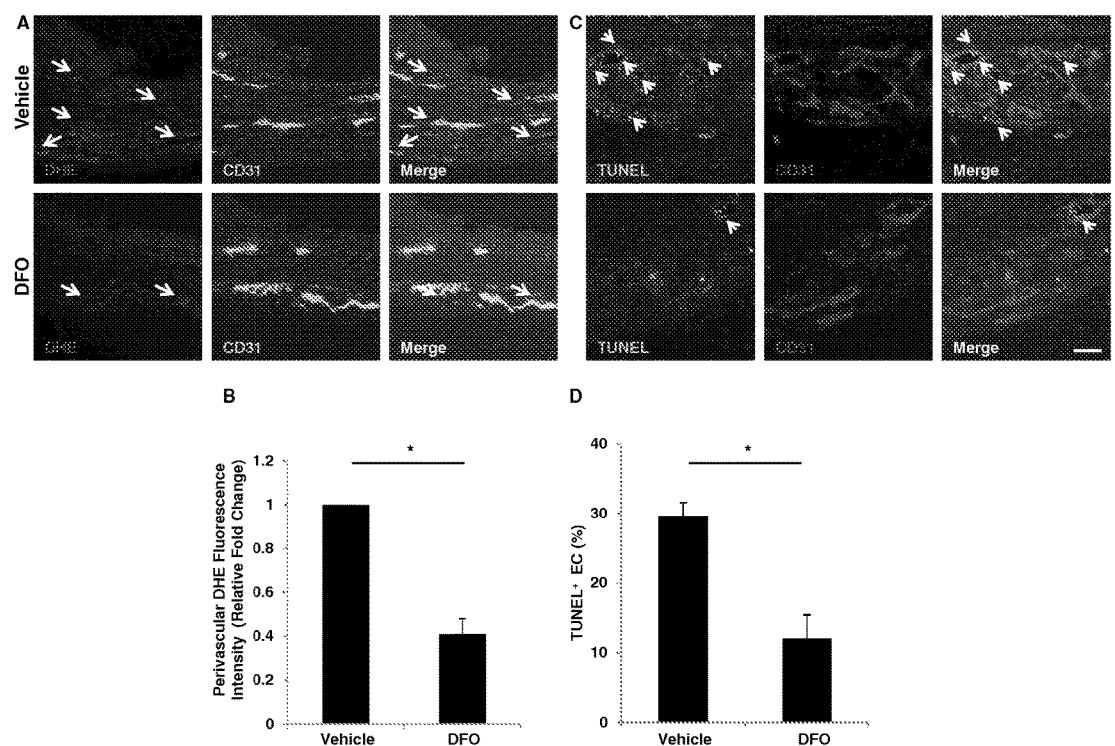
FIG. 8. Decreased levels of perivascular ROS production and endothelial cell apoptosis in DFO treated tracheas. A, C. Confocal microscopic images showing decreased perivascular ROS production by DHE staining (red, white arrows) and EC apoptosis by TUNEL staining (green, white arrows). B, D. Quantification of perivascular DHE staining and EC TUNEL staining (n=3-5). Scale bars: 20 µm (A, C). Data are shown as means±SEM. *P<0.05, Student's t test (B, D).

Endothelial nitric oxide synthase (eNOS) phosphorylation is associated with endothelial cell survival and angiogenesis. We hypothesized that DFO may increase eNOS phosphorylation in this transplantation model system. Examination of endothelial phosphorylated eNOS (p-eNOS) expression in d3 allograft showed that DFO treatment increased p-eNOS expression by about 2 fold (FIG. 7A, B). EC proliferation, measured by Ki67 staining, in DFO treated allografts was much higher than that of the vehicle treated samples (about 30% vs 15%) (FIG. 7C, D). Production of ROS in ischemic tissue is associated with EC death. Dihydroethidium (DHE) staining showed that DFO treated allograft exhibited much lower levels of perivascular ROS production (FIG. 8A, B). Lastly, the TUNEL assay showed that DFO treatment significantly decreased EC apoptosis (FIG. 8C, D). These data together suggested that DFO may also improve airway microvascular perfusion by augmenting angiogenesis through the promotion of EC proliferation and prevention of EC apoptosis.

Possibly because current practice omits bronchial artery revascularization at the time of surgery, large airway tissue ischemia is a common finding post-operatively and creates risk for developing anastomotic complications in human lung transplantation. We have previously shown that augmenting HIF-1α expression in donor grafts by either adenovirus-mediated gene therapy or knockdown of the VHL expression in recipient-derived Tie2 expressing cells was able to promote airway microvascular regeneration and diminish airway ischemia. In the current study, we sought to develop a nanoparticle formulation of DFO, an FDA-approved drug to augment the local expression levels of HIF-1α and ameliorate airway ischemia.

We started with the characterization of the biophysical properties of DFO nanoparticles by utilizing various techniques. Raman spectroscopy structure analysis and imaging showed that DFO encapsulation by lecithin was very efficient. Next, the SEM morphological study of the dry nanoparticle powder showed that the DFO formulation was also homogeneous. Lastly, confocal microscopy showed a very high percentage of drug-positive cells in tracheas treated with the DFO nanoparticles. Consistent with these, in vitro identified superior biophysical properties, the DFO nanoparticles were highly effective in promoting airway microvascular perfusion at both d3 and d10 following transplantation. Our data suggest that combination of the usage of Raman spectroscopy, SEM imaging, AFM imaging, confocal microscopy and HPLC-MS analysis can efficiently characterize biophysical and biological properties of the lecithin nanoparticle formulations. Nanoparticles with more efficient encapsulation, better tissue penetration and retention are likely to display higher bioactivity in vivo.

Prior to the formation of the microvascular anastomosis between the graft donor and the recipient, the airway allograft is not perfused. Therefore, improved d3 microvascular perfusion is a result of enhanced donor-recipient microvascular anastomosis formation. In clinical lung transplantation, early post-operative airway ischemia is observed as a result of delayed microvascular anastomosis formation and sacrifice of the bronchial circulation. Thus, the effect of DFO nanoparticles on promoting airway microvascular anastomosis formation may have clinical relevance in terms of alleviating tissue ischemia with the potential to diminish airway complications. Airway ischemia has also been shown to be a risk factor for anastomotic bacterial and fungal overgrowth, which often further increases the risk of the development of airway complications. We recently demonstrated that *Aspergillus fumigatus* airway invasion could be attenuated in transplant recipients with genetically-upregulated HIF-1α levels that resulted in better airway allograft perfusion. These data together suggest that DFO nanoparticles may limit airway complications through alleviating tissue ischemia and diminishing relevant microbial infection.

DFO is a bacterial siderophore produced by the Actinobacteria *Streptomyces pilosus*. Because DFO depletes iron, it is generally used as an iron-chelating drug to treat iron overload conditions. Recent studies suggest that, DFO also promotes angiogenesis and alleviates tissue ischemia in animal models. This property of DFO is generally thought to be due to its ability to stabilize HIF-1α through the inhibition of prolyl 4-hydroxylase by chelation of iron from enzyme's catalytic center. In this study, we found that DFO treated airway grafts expressed significantly higher levels of PLGF and SDF-1, but no significant difference was noted in the expression of VEGF, ANGPT1 and ANGPT2. The increase in expression levels of PLGF and SDF-1 with DFO is consistent with our previous study utilizing adenovirus-mediated HIF-1α gene therapy. HIF-1 activates transcription of the gene encoding SDF-1, and increased SDF-1 expression promotes vascular regeneration by enhancing recruitment of CXCR4-expressing angiogenic cells. While other studies have shown that VEGF is often upregulated following DFO treatment, the DFO nanoparticles in this study did not increase VEGF expression in d3 allografts. This suggests that DFO may promote airway anastomotic microvascular formation mainly through PLGF-mediated signaling. It is likely that PLGF, like SDF1, serves as a chemotactic factor for the recruitment of bone marrow-derived angiogenic cells. PLGF is a member of the VEGF family of growth factors, but unlike VEGF, PLGF is not required for vascular development and homeostasis; PLGF has diverse non-redundant roles in various physiological or pathological status such as tissue ischemia, inflammation and malignancy. PLGF is also considered a protective paracrine effector in the heart and was recently shown to promote myocardial blood flow and contractile function in chronic myocardial ischemia by increasing neovascularization. PLGF has also been shown to enhance endothelial cell proliferation, migration and survival. Consistent with these studies, we observed increased expression of Ki67 in DFO nanoparticles treated tracheal endothelial cells, supporting the notion that, in this airway transplantation model, PLGF may promote airway anastomotic microvascular formation through stimulating endothelial cell proliferation and subsequent angiogenesis. However, we cannot rule out alternative mechanisms by which PLGF may promote angiogenesis, such as recruiting myeloid progenitor cells which facilitate the growth of vascular sprouts has been suggested.

DFO treatment significantly increased the levels of the p-eNOS. eNOS is activated/phosphorylated by the PI3K-Akt pathway. Interestingly, PLGF has been shown to enhance Akt activation in endothelial cells to promote their proliferation and migration and has also been shown to activate Akt in monocytes. Recent studies showed that PLGF is a direct HIF target gene and that it dilates mesenteric arteries through NO production. It is therefore likely that, in this airway transplantation model, DFO increased p-eNOS through PLGF activated PI3K-Akt pathway.

ROS are known to cause endothelial cell dysfunction, and increased ROS production promotes eNOS uncoupling, which is a significant contributor to oxidative stress. Iron participates in the redox reactions that lead to the production of ROS, and the reduction of ROS by iron chelation has been shown to be an effective therapy for atherosclerosis. These studies suggest that endothelial cell damage may be promoted by a feed-forward cycle of eNOS dysfunction leading to ROS production which leads to further eNOS dysfunction. In airways treated with DFO, we observed a reduction in ROS production concomitantly with increased levels of p-eNOS; this finding suggests that through its iron-chelating activity, DFO may prevent or at least ameliorate endothelial cell injury through reducing oxidative stress by enhancing the function of eNOS. In summary, DFO augmented airway anastomotic microvascular regeneration through the production of angiogenic factors as well as reduction of ROS, which improved overall endothelial cell health and decreased airway ischemia.

We have successfully developed a lipid-based, biologically-compatible nanoparticle formulation that can effectively improve tracheal anastomotic microvascular formation and airway microvascular repair following initial surgical injury as well as alloimmune injury. The DFO nanoparticle formulation improves airway blood flow through the production of angiogenic growth factors as well as reduction of the production of ROS. As airway anastomotic complications continue to be a cause of morbidity and mortality in lung transplants patients, our DFO nanoparticle formulation may be a promising therapy for diminishing airway ischemia and thereby preventing airway complications. The current study also provided a proof-of-concept result, which shows that airway ischemia and complications can be limited through augmenting anastomotic HIF-1α expression by using iron chelators.

What is claimed is:

1. A method of reducing graft failure following lung transplantation by improving microvascular perfusion and anastomosis formation, the method comprising:

topically painting at least one inner or outer surface involved in anastomosis of a lung for transplantation with an effective dose of a nanoparticle formulation comprising:

iron chelator nanoparticles wherein the iron chelator is selected from deferoxamine (DFO) and deferasirox (DFX) and is stabilized with lecithin and phospholipids as a stabilizer, wherein the nanoparticle comprises from about 40% to about 60% by weight active agent, and suspended at a concentration of from about 5% to about 25% nanoparticles as weight/volume in a physiologically acceptable oil comprising medium chain triglycerides compatible with lung tissue;

wherein airway graft microvascular perfusion and anastomosis formation in the lung is increased at by 10 days following transplantation relative to an untreated airway; and graft failure is reduced.

2. The method of claim 1, wherein the stabilizer further comprises protein.

3. The method of claim 1, wherein the stabilizer comprises a mixture of protein, and a cationic lipid in a ratio of from about 1:15 to 1:5 by weight.

4. The method of claim 1, wherein the nanoparticles are formed by precipitation of the iron chelating agent and pharmaceutically acceptable stabilizer from a liquid suspension.

5. The method of claim 1, wherein the nanoparticles have a diameter of from about 10 nm to about 5 μm.

6. The method of claim 5, wherein the nanoparticles have a diameter of from about 100 nm to about 5 μm.

7. The method of claim 1, wherein the carrier provides for nanoparticle penetration to a depth of at least about 1 mm over a period of time up to about 30 minutes.

* * * * *